(12) United States Patent
Li et al.

(10) Patent No.: US 12,016,377 B2
(45) Date of Patent: Jun. 25, 2024

(54) ELECTRONIC CIGARETTE AND ATOMIZER THEREOF WITH HEATING ASSEMBLY

(71) Applicant: SHENZHEN SMOORE TECHNOLOGY LIMITED, Shenzhen (CN)

(72) Inventors: Xiaoping Li, Shenzhen (CN); Changyong Yi, Shenzhen (CN); Zhenlong Jiang, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 145 days.

(21) Appl. No.: 17/196,971

(22) Filed: Mar. 9, 2021

(65) Prior Publication Data

US 2021/0186088 A1 Jun. 24, 2021

Related U.S. Application Data

(63) Continuation of application No. 15/983,108, filed on May 18, 2018, now Pat. No. 10,973,262.

(30) Foreign Application Priority Data

Feb. 13, 2018 (CN) .......................... 201810150690.7

(51) Int. Cl.
*A24F 40/46* (2020.01)
*A24F 1/00* (2006.01)
(Continued)

(52) U.S. Cl.
CPC ................ *A24F 1/00* (2013.01); *A24F 40/46* (2020.01); *A24F 40/485* (2020.01); *A24F 47/00* (2013.01);
(Continued)

(58) Field of Classification Search
CPC .. A24F 1/00; A24F 40/10; A24F 40/46; A24F 40/485; A24F 47/00;
(Continued)

(56) References Cited

U.S. PATENT DOCUMENTS 9,289,014 B2    3/2016  Tucker et al.
9,603,389 B2 *  3/2017  Chen ..................... A24F 40/485
(Continued)

FOREIGN PATENT DOCUMENTS

CA    3022340 A1   11/2017
CN    103960782 A   8/2014
(Continued)

OTHER PUBLICATIONS

European Patent Office Search Report for Appl. No. 18174503.5-1122, European Patent Office, dated Jan. 4, 2019.
(Continued)

*Primary Examiner* — Abdullah A Riyami
*Assistant Examiner* — Thang H Nguyen
(74) *Attorney, Agent, or Firm* — Andrew C. Cheng

(57) ABSTRACT

The present disclosure provides an electronic cigarette atomizer, including an atomization assembly and a liquid reservoir engaging with the atomization assembly; the liquid reservoir includes a liquid storage cavity; wherein the atomization assembly includes a lower holder, an upper holder installed on the lower holder, and a heating assembly clamped between the lower and the upper holders; the heating assembly includes a porous body and at least one heater engaging with the porous body, and the porous body has an atomizing surface and a liquid-absorbing surface; and the liquid-absorbing surface communicates with the liquid storage cavity, and an atomization cavity is formed between the atomizing surface and the lower holder. In the present disclosure, the heating assembly is a porous body and is (Continued)

clamped by the upper holder and the lower holder, thus, the structure is stable and the assembly of the heating assembly is facilitated.

33 Claims, 14 Drawing Sheets

(51) Int. Cl.
*A24F 40/485* (2020.01)
*A24F 47/00* (2020.01)
*A61M 11/04* (2006.01)
*A61M 15/06* (2006.01)
*C04B 35/00* (2006.01)
*A24F 40/10* (2020.01)
*H05B 3/12* (2006.01)
*H05B 3/22* (2006.01)

(52) U.S. Cl.
CPC .......... *A61M 11/042* (2014.02); *A61M 15/06* (2013.01); *C04B 35/00* (2013.01); *A24F 40/10* (2020.01); *A61M 2205/3653* (2013.01); *H05B 3/12* (2013.01); *H05B 3/22* (2013.01); *H05B 2203/003* (2013.01); *H05B 2203/021* (2013.01)

(58) Field of Classification Search
CPC ...... G05B 19/0425; G05B 2219/25067; G05B 23/0216; A61M 11/042; A61M 15/06; A61M 2205/3653; H05B 2203/003; H05B 2203/021; H05B 3/12; H05B 3/22
See application file for complete search history.

(56) References Cited

U.S. PATENT DOCUMENTS

| | | | |
|---|---|---|---|
| 9,795,168 B2 * | 10/2017 | Zhu | A24F 40/46 |
| 9,814,269 B2 * | 11/2017 | Li | H05B 3/44 |
| 9,861,129 B2 * | 1/2018 | Liu | C04B 35/14 |
| 9,877,516 B2 | 1/2018 | Tucker et al. | |
| 10,687,557 B2 * | 6/2020 | Tucker | A24F 47/00 |
| 10,973,262 B2 | 4/2021 | Li | |
| 2015/0189919 A1 | 7/2015 | Liu | |
| 2016/0073692 A1 | 3/2016 | Alarcon | |
| 2016/0106153 A1 | 4/2016 | Zhu | |
| 2016/0143358 A1 | 5/2016 | Zhu | |
| 2016/0192707 A1 | 7/2016 | Li | |
| 2016/0309785 A1 * | 10/2016 | Holtz | B65D 53/04 |
| 2016/0353802 A1 * | 12/2016 | Malgat | A24F 40/42 |
| 2017/0105455 A1 * | 4/2017 | Qiu | A24F 40/485 |
| 2017/0112193 A1 | 4/2017 | Chen | |
| 2017/0150755 A1 | 6/2017 | Batista | |
| 2017/0215481 A1 | 8/2017 | Li et al. | |
| 2017/0340012 A1 | 11/2017 | Mironov | |
| 2017/0340015 A1 | 11/2017 | Thorens | |
| 2018/0035720 A1 | 2/2018 | Qiu | |
| 2018/0184714 A1 | 7/2018 | Liu | |
| 2019/0046745 A1 * | 2/2019 | Nettenstrom | A61M 11/042 |
| 2019/0099562 A1 * | 4/2019 | Nettenstrom | A61M 15/0021 |
| 2019/0350263 A1 * | 11/2019 | Qiu | A24F 40/49 |
| 2019/0364972 A1 * | 12/2019 | Lin | A24F 40/40 |
| 2020/0260787 A1 | 8/2020 | Zinovik | |
| 2020/0352238 A1 * | 11/2020 | Simpson | A24F 40/42 |
| 2020/0367564 A1 | 11/2020 | Li | |
| 2020/0397043 A1 | 12/2020 | Li | |
| 2021/0000179 A1 | 1/2021 | Li | |
| 2021/0000181 A1 | 1/2021 | Li | |

FOREIGN PATENT DOCUMENTS

| | | |
|---|---|---|
| CN | 203851804 U | 10/2014 |
| CN | 204070542 U | 1/2015 |
| CN | 104522891 A | 4/2015 |
| CN | 204317489 U | 5/2015 |
| CN | 104824853 A | 8/2015 |
| CN | 204796739 U | 11/2015 |
| CN | 204949517 U | 1/2016 |
| CN | 105294140 A | 2/2016 |
| CN | 105310114 A | 2/2016 |
| CN | 105394816 A | 3/2016 |
| CN | 105418070 A | 3/2016 |
| CN | 105433446 A | 3/2016 |
| CN | 205106385 U | 3/2016 |
| CN | 105768229 A | 7/2016 |
| CN | 205512338 U | 8/2016 |
| CN | 205624481 U | 10/2016 |
| CN | 106136327 A | 11/2016 |
| CN | 205695698 U | 11/2016 |
| CN | 205813574 U | 12/2016 |
| CN | 206062123 U | 4/2017 |
| CN | 206062138 U | 4/2017 |
| CN | 206079042 U | 4/2017 |
| CN | 106723372 A | 5/2017 |
| CN | 106820269 A | 6/2017 |
| CN | 106820272 A | 6/2017 |
| CN | 206260849 U | 6/2017 |
| CN | 206390306 U | 8/2017 |
| CN | 107182139 A | 9/2017 |
| CN | 206507320 U | 9/2017 |
| CN | 206518143 U | 9/2017 |
| CN | 206525553 U | 9/2017 |
| CN | 206729208 U | 12/2017 |
| CN | 206729211 U | 12/2017 |
| CN | 206808661 U | 12/2017 |
| CN | 207978957 U | 10/2018 |
| CN | 207978958 U | 10/2018 |
| CN | 207978959 U | 10/2018 |
| CN | 208048028 U | 11/2018 |
| CN | 208113970 U | 11/2018 |
| CN | 105394816 B | 12/2018 |
| EP | 2574247 A1 | 4/2013 |
| EP | 2946678 A1 | 11/2015 |
| EP | 3020292 A1 | 5/2016 |
| EP | 3099190 A1 | 12/2016 |
| EP | 3162778 A1 | 5/2017 |
| EP | 3188570 A2 | 7/2017 |
| EP | 3200559 A2 | 8/2017 |
| EP | 3099190 B1 | 11/2018 |
| EP | 2946678 B1 | 7/2019 |
| EP | 3524069 A1 | 8/2019 |
| EP | 3569072 A1 | 11/2019 |
| EP | 3524069 B1 | 12/2022 |
| GB | 2504074 A | 1/2014 |
| JP | 2007117970 A | 5/2007 |
| WO | 2014079024 A1 | 5/2014 |
| WO | 2014151040 A2 | 9/2014 |
| WO | 2016107767 A1 | 7/2016 |
| WO | 2016119170 A1 | 8/2016 |
| WO | 2016154792 A1 | 10/2016 |
| WO | 2016161554 A1 | 10/2016 |
| WO | 2016169115 A1 | 10/2016 |
| WO | WO-2016169115 A1 * | 10/2016 ............. A24F 47/00 |
| WO | 2016198417 A1 | 12/2016 |
| WO | 2017005471 A1 | 1/2017 |
| WO | 2017163050 A1 | 9/2017 |
| WO | 2017163051 A1 | 9/2017 |
| WO | 2017163052 A1 | 9/2017 |
| WO | 2017187148 A1 | 11/2017 |
| WO | 2018007965 A1 | 1/2018 |
| WO | 2018019485 A1 | 2/2018 |
| WO | 2018172765 A1 | 9/2018 |
| WO | WO-2018172765 A1 * | 9/2018 ............. A24F 40/10 |

OTHER PUBLICATIONS

European Patent Office Communications under Art. 94(3) EPC re Appl. No. 18174503.5-1122, European Patent Office, dated Apr. 30, 2021.

PCT Search report with translation of PCT application No. PCT/CN2018/076694 dated Sep. 20, 2018.

(56) References Cited

OTHER PUBLICATIONS

PCT written opinion of the international searching authority with translation of PCT application No. PCT/CN2018/076694 dated Sep. 20, 2018.
Notice of Allowance of U.S. Appl. No. 15/983,108 dated Jan. 1, 2021.
Non-Final OA of U.S. Appl. No. 15/983,108 issued on Jul. 10, 2020.
Final OA of U.S. Appl. No. 15/983,108 issue on Nov. 6, 2020.
Communication pursuant to Article 94(3) EPC of EP application No. 18174503.5-1122 dated Mar. 12, 2021.
Office action with search report and its translation of CN application No. 201810150690.7 dated Mar. 27, 2019.
Office action with search report and its translation of CN application No. 201810150690.7 dated Aug. 14, 2019.
Non-Final OA of U.S. Appl. No. 17/189,904 issued on Dec. 23, 2022.
Non-Final OA of U.S. Appl. No. 17/198,511 issued on Feb. 15, 2023.
Non-Final OA of U.S. Appl. No. 17/199,828 issued on Feb. 15, 2023.
Communication under Rule 71(3) EPC with grant text of EP application No. 18174503.5 dated Jul. 5, 2022.
Notice of Allowance with search report of CN application No. 201810150690.7 dated Dec. 10, 2019.
Evaluation report of CN application No. 201820260617.0 dated Oct. 19, 2019.
Supplementary European search report of EP application No. 18905927.2 dated Jul. 30, 2021.
The extended European search report of EP application No. 18906272.2 dated Aug. 6, 2021.
The extended European search report of EP application No. 18906621.0 dated Jul. 12, 2021.
The reexamination decision of CN application No. 201810150539.3 dated Jul. 16, 2020.
The reexamination decision of CN application No. 201810150549.7 dated Mar. 31, 2022.
The reexamination decision of CN application No. 201810150560.3 dated Jul. 16, 2020.
The reexamination decision of CN application No. 201810150677.1 dated Apr. 8, 2022.
Notice of Allowance of CN application No. 201810150539.3 dated Aug. 24, 2020.
Notice of Allowance of CN application No. 201810150549.7 dated Apr. 28, 2022.
Notice of Allowance of CN application No. 201810150677.1 dated Apr. 21, 2022.
Notice of Allowance of CN application No. 201810150560.3 dated Aug. 13, 2020.
The first OA and Search report of CN application No. 201810150539.3 dated Mar. 22, 2019.
The first OA and Search report of CN application No. 201810150549.7 dated Mar. 22, 2019.
The first OA of CN application No. 201810150677.1 issued on Mar. 25, 2019.
The Search report of CN application No. 201810150677.1 dated Mar. 25, 2019.
The Search report of CN application No. 201810150560.3 dated Mar. 25, 2019.
The first OA of CN application No. 201810150560.3 issued on Mar. 25, 2019.
The second OA of CN application No. 201810150539.3 issued on Sep. 27, 2019.
The second OA of CN application No. 201810150549.7 issued on Dec. 25, 2019.
The Search report of CN application No. 201810150560.3 dated Dec. 25, 2019.
The second OA of CN application No. 201810150560.3 issued on Dec. 25, 2019.
The second OA and Search report of CN application No. 201810150677.1 dated Nov. 26, 2019.
International Search Report of PCT Patent Application No. PCT/CN2018/076688 dated Sep. 10, 2018.
International Search Report of PCT Patent Application No. PCT/CN2018/076691 dated Oct. 18, 2018.
International Search Report of PCT Patent Application No. PCT/CN2018/076692 dated Oct. 25, 2018.
International Search Report of PCT Patent Application No. PCT/CN2018/076695 dated Oct. 23, 2018.
Written opinion of PCT Patent Application No. PCT/CN2018/076688 dated Sep. 10, 2018.
Written opinion of PCT Patent Application No. PCT/CN2018/076691 dated Oct. 18, 2018.
Written opinion of PCT Patent Application No. PCT/CN2018/076692 dated Oct. 25, 2018.
Written opinion of PCT Patent Application No. PCT/CN2018/076695 dated Oct. 23, 2018.
Notice of Reexamination of CN application No. 201810150549.7 dated Nov. 5, 2021.
Notice of Reexamination of CN application No. 201810150677.1 dated Nov. 5, 2021.
Rejection decision of CN application No. 201810150539.3 dated Mar. 19, 2020.
Rejection decision of CN application No. 201810150549.7 dated Apr. 20, 2020.
Rejection decision of CN application No. 201810150560.3 dated Mar. 19, 2020.
Rejection decision of CN application No. 201810150677.1 dated Apr. 22, 2020.
The extended European search report of EP application No. 23157027.6 issued on Apr. 5, 2023.
The extended European search report of EP application No. 22212991.8 issued on Apr. 5, 2023.
Notice of Allowance of the U.S. Appl. No. 17/189,904 issued on Jun. 15, 2023.
Non-Final OA of U.S. Appl. No. 16/969,653 issued on Aug. 11, 2020.
Non-Final OA of U.S. Appl. No. 16/969,686 issued on Aug. 14, 2020.
Non-Final OA of U.S. Appl. No. 16/969,828 issued on Aug. 30, 2020.
Communication pursuant to Article 94(3) EPC of EP patent application No. 18905927.2 issued on Jul. 19, 2023.
Communication pursuant to Article 94(3) EPC of EP patent application No. 18906621.0 issued on Jul. 20, 2023.
Notice of Allowance of U.S. Appl. No. 17/189,904 issued on Jun. 15, 2023 and Jul. 31, 2023.
Notice of Allowance of U.S. Appl. No. 17/198,511 issued on Jul. 28, 2023.
Notice of Allowance of U.S. Appl. No. 17/199,828 issued on Aug. 1, 2023.
Non-Final OA of U.S. Appl. No. 16/969,800 issued on Sep. 28, 2023.
Notice of Allowance of U.S. Appl. No. 16/969,686 issued on Oct. 3, 2023.
Communication of a notice of opposition of EP application No. 18174503.5 issued on Sep. 19, 2023.
Communication of a notice of opposition of EP application No. 18174503.5 issued on Sep. 20, 2023.
The extended European search report of EP application No. 189063795 issued on Aug. 10, 2021.
The extended European search report of EP application No. 189059272 issued on Jul. 13, 2021.

* cited by examiner

ELECTRONIC CIGARETTE AND ATOMIZER THEREOF WITH HEATING ASSEMBLY

TECHNICAL FIELD

The present disclosure generally relates to devices for smokers, and more particularly, to an electronic cigarette and an atomizer thereof.

BACKGROUND

Electronic cigarettes are also known as virtual cigarettes or electronic atomizers. As substitutes for conventional cigarettes, the electronic cigarettes are often used for quitting smoking. With similar appearance and flavor to conventional cigarettes, the electronic cigarettes are generally free of harmful chemicals like tar in the cigarettes or aerosol. A typical electronic cigarette includes an atomizer and a battery assembly. At present, the atomizer mostly includes a fiber rope to guiding e-liquid and a heating coil wound around the fiber rope, which to some extent can realize the function of the electronic cigarettes. However, it's difficult to fasten the heating coil in the assembling process of the electronic cigarette, which leads to inefficiency of installation of the electronic cigarette and low rate of finished products.

Technical Problem

Therefore, the present disclosure aims to provide an improved electronic cigarette and an atomizer thereof.

SUMMARY OF THE DISCLOSURE

An electronic cigarette atomizer provided in the present disclosure includes an atomization assembly and a liquid reservoir engaging with the atomization assembly; the liquid reservoir includes a liquid storage cavity; wherein the atomization assembly includes a lower holder, an upper holder installed on the lower holder, and a heating assembly clamped between the lower and the upper holders; the heating assembly includes a porous body and at least one heater engaging with the porous body, and the porous body has an atomizing surface and a liquid-absorbing surface; and the liquid-absorbing surface communicates with the liquid storage cavity, and an atomization cavity is formed between the atomizing surface and the lower holder.

In an embodiment, the atomization assembly includes a first intake channel and a first exhaust channel respectively communicating with the atomization cavity; the first intake channel communicates with the external environment, and the first intake channel and the first exhaust channel are formed in the lower holder; the atomization assembly includes a second intake channel communicating with the first exhaust channel, a connecting channel communicating with the second intake channel, and a second exhaust channel communicating with the connecting channel; and the second intake channel, the connecting channel and the second exhaust channel are formed in the upper holder.

In an embodiment, an air intake of the first intake channel is higher than the atomization cavity.

In an embodiment, the liquid reservoir includes an airflow tube communicating with the second exhaust channel and an air outlet communicating with the airflow tube.

In an embodiment, the lower holder includes a base and a supporting structure arranged on the base; the heating assembly is arranged on the supporting structure; and the atomizing surface faces the base and is spaced from the base at an interval which forms the atomization cavity.

In an embodiment, the base is clamped to the liquid reservoir.

In an embodiment, the supporting structure includes a first supporting arm and a second supporting arm arranged on a top surface of the base, and the second supporting arm corresponds to the first supporting arm; and the heating assembly is arranged between the first supporting arm and the second supporting arm, and the first supporting arm is symmetrical about the second supporting arm.

In an embodiment, the first supporting arm and the second supporting arm are respectively clamped to the upper holder.

In an embodiment, the atomization assembly includes a sleeving cover which has two second blocking arms respectively engaging with the first supporting arm and the second supporting arm to form the first intake channel and the first exhaust channel; and a first air intake communicating with the first intake channel is formed in the second blocking arm corresponding to the first intake channel.

In an embodiment, the upper holder includes a main body, and the second intake channel and the second exhaust channel are separately formed on the main body; a slot channel communicating with the second intake channel and the second exhaust channel is formed on the sidewall of the main body; the atomization assembly includes a sleeving cover which includes a first blocking arm covering the slot channel to form the connecting channel.

In an embodiment, the upper holder includes a main body and a liquid channel running through the main body and communicating with the liquid-absorbing surface and the liquid storage cavity.

In an embodiment, the upper holder includes a main body and an embedded portion extending downwards from the main body; the embedded portion is sleeved on the heating assembly; and the atomization assembly also includes a sealing member arranged between the embedded portion and the heating assembly.

In an embodiment, the liquid reservoir includes a liquid storage unit and a sleeving portion connected to the liquid storage unit; the liquid storage cavity is formed between the liquid storage unit and the airflow tube; the sleeving portion is sleeved on the atomization assembly; two second air intakes communicating with the first intake channel are respectively formed in a left side and a right side of the sleeving portion, and the sleeving portion is symmetrically configured.

In an embodiment, a fool-proofing structure is arranged between the sleeving cover and the upper holder such that the first air intake corresponds to the first intake channel in the assembling process of the electronic cigarette atomizer.

In an embodiment, the at least one heater includes an elongated sheet heating unit; at least one part of at least one section of the sheet heating unit is inbuilt in the porous body; and at least one section of the sheet heating unit corresponds to the atomizing surface.

In an embodiment, the at least one section of the elongated sheet heating unit is inbuilt in the porous body in a width direction and following a moving direction of e-liquid and/or smoke.

In an embodiment, the at least one section of the sheet heating unit is substantially perpendicular to a plane where the atomizing surface is located in the width direction.

In an embodiment, the liquid-absorbing surface of the porous body is recessed to form a groove, the liquid-absorbing surface is defined on an inner surface of a bottom wall of the porous body, and the atomizing surface is defined on an outer surface of the bottom wall of the porous body.

In an embodiment, the atomization assembly includes a magnetic assembly arranged on the lower holder.

The present disclosure further provides an electronic cigarette having the above electronic cigarette atomizer.

In the present disclosure, the heating assembly is a porous body and is clamped by the upper holder and the lower holder, thus, the structure is stable and the assembly of the heating assembly is facilitated.

BRIEF DESCRIPTION OF THE DRAWINGS

The present disclosure will be described in more detail with reference to the accompany drawings and the embodiments, wherein in the drawings.

PREFERRED EMBODIMENTS

The preferred embodiments are illustrated in detail with reference to the attached drawings so as to have a clearer understanding of the technical characteristics, purpose and effect of the present disclosure.

Figure 1:
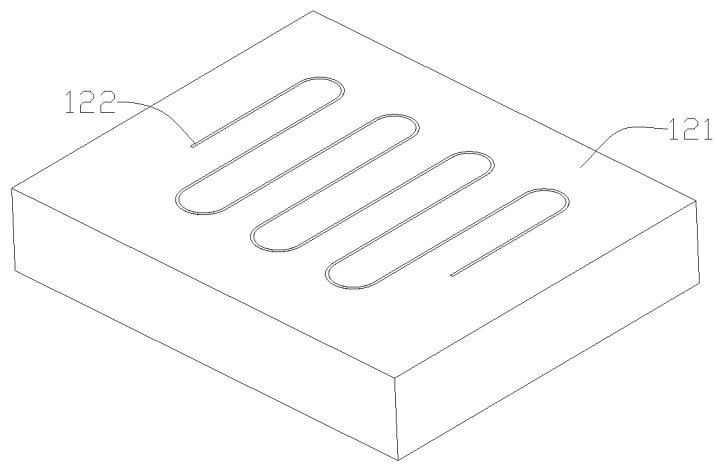
FIG. 1 is a three-dimension assembled view of a heating assembly in accordance with an embodiment of the present disclosure.
Figure 2:
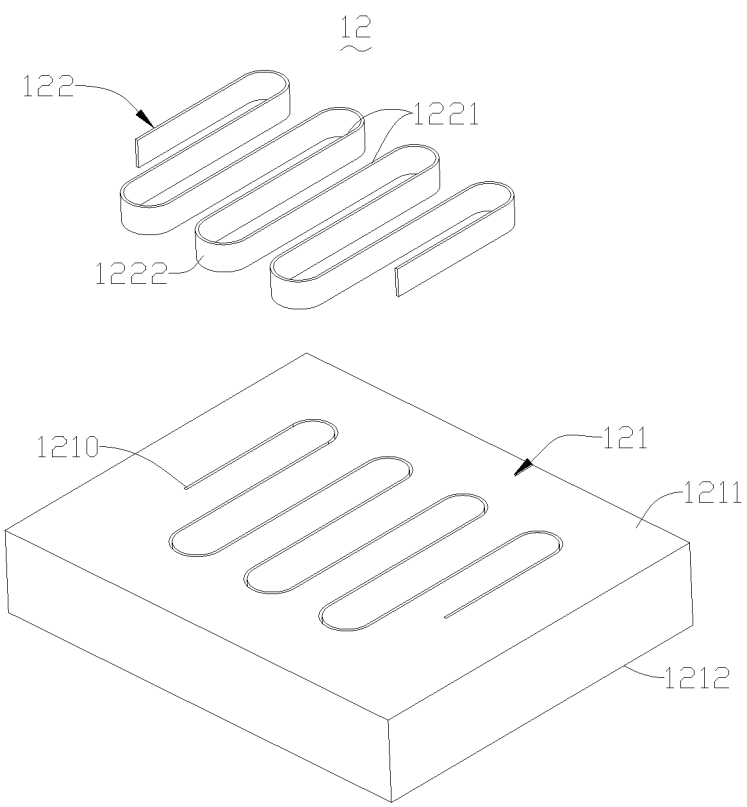
FIG. 2 is a three-dimension exploded view of the heating assembly of FIG. 1 in accordance with an embodiment of the present disclosure.
Figure 3:
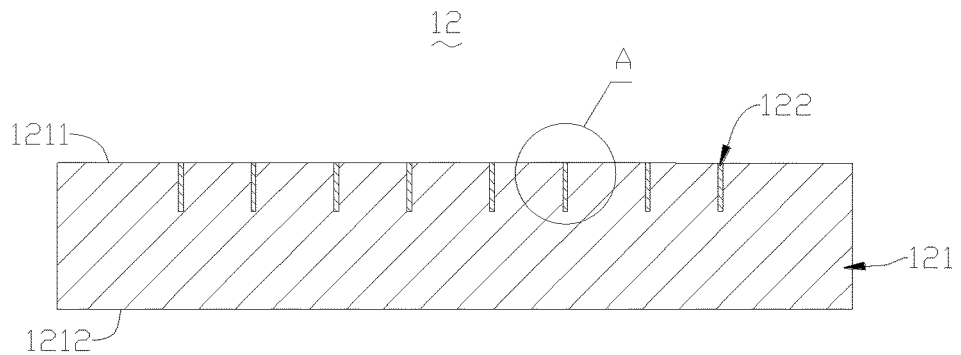
FIG. 3 is a longitudinal cross-sectional view of the heating assembly of FIG. 1 in accordance with an embodiment of the present disclosure.

A heating assembly 12 of an electronic cigarette in some embodiments of the present disclosure is shown from FIG. 1 to FIG. 3. The heating assembly 12 can be applied in an atomizer of the electronic cigarette to heat and atomize e-liquid. The heating assembly 12 includes a porous body 121 for absorbing the e-liquid from a liquid storage cavity of the atomizer and a heater 122 for heating and atomizing the e-liquid absorbed by the porous body 121. The heater 122 includes an elongated sheet heating unit which is embedded in the porous body 121. All or most of a surface area of the sheet heating unit contacts the porous body 121, which has the effect of high atomized efficiency, low loss of heat, and dry burning prevention or protection, etc.

In an embodiment, the sheet heating unit is inbuilt in the porous body 121 in a width direction and following a moving direction of the e-liquid and/or smoke, which can not only make the movement of the e-liquid and/or smoke smoother, but also centralize more heat around an atomizing surface 1211 to improve the availability of the heat rather than deliver more heat towards a liquid-absorbing surface 1212 along the opposite direction. The porous body 121, in some embodiments, can be made of hard capillary structure like porous ceramics, porous glass ceramics, porous glass and so on. The sheet heating unit of the heater 122, in some embodiments, can be made of stainless steel, nichrome, iron-chromium-aluminum alloy, titanium and so on.

When the porous body 121 has a sintering structure, the sheet heating unit of the heater 122 can be integrally formed with the heating unit of the porous body 121 by sintering. In an embodiment which the porous body 121 is made of the porous ceramics, when the sheet heating unit is a metal sheet, a base of the porous body 121 is at first formed using the Kaolin mud, and then the sheet heating unit of the heater 122 is embedded into the base which is baked and sintered thereafter. When the sheet heating unit is a coated sheet heating unit, the sheet heating unit can be coated on an organic diaphragm and the organic diaphragm is embedded into the base which is baked and sintered thereafter. The organic diaphragm is burnt off in the sintering process, leaving the coated sheet heating unit combined with the porous body closely.

Compared with a heating coil, the sheet heating unit has a larger surface area. Under the circumstance of satisfying certain mechanical properties, a thickness of the sheet heating unit can be greatly smaller than a diameter of the heating coil (the heating coil with too small diameter is easily burnt off). Therefore, the sheet heating unit can be very thin to lead to low internal accumulation of heat and high atomized efficiency. For example, the thickness of the sheet heating unit, in some embodiments, can be from 0.04 mm to 0.1 mm and a width of the sheet heating unit can be from 0.3 mm to 0.6 mm. In some embodiments, the thickness of the sheet heating unit can be even smaller to reach about 0.008 mm.

The porous body 121 in some embodiments can be but not limited to be in the shape of rectangle. The porous body 121 includes the atomizing surface 1211 and the liquid-absorbing surface 1212 parallel to the atomizing surface 1211. The liquid-absorbing surface 1212 is used to communicate with the liquid storage cavity such that the e-liquid can flow into the porous body 121. The e-liquid is heated and atomized in the porous body 121 and then escape through the atomizing surface 1211. The porous body 121 further includes a receiving groove 1210 for receiving the sheet heating unit of the heater 122. The receiving groove 1210 extends parallel to a plane which is parallel to the atomizing surface 1211 in a length direction, while extends away from the atomizing surface 1211 in a depth direction.

In some embodiments, because the liquid-absorbing surface 1212 is parallel to the atomizing surface 1211, the moving directions of the e-liquid and smoke in the porous body 121 are vertical to a plane where the atomizing surface 1211 is located. A depth direction of the receiving groove 1210 is vertical to the plane where the atomizing surface 1211 is located so that when the sheet heating unit of the heater 122 is received in the receiving groove 1210, the width direction is also vertical to the plane where the atomizing surface 1211 is located. When the width direction of the sheet heating unit of the heater 122 is vertical to the atomizing surface 1211, on the one hand the e-liquid and the smoke will move more smoothly in the porous body 121, on the other hand the manufacture of the heater 122 will be facilitated. In addition, main heat conduction sides (front and back surfaces of the sheet heating unit defined by the length and the width) of the sheet heating unit of the heater 122 are located laterally to heat the e-liquid close to the atomizing surface 1211 and thus improve the atomized efficiency. Besides, as the sheet heating unit of the heater 122 is thin, and an upper surface and a lower surface defined by the thickness and the length are both small, the e-liquid away from the atomizing surface 1211 absorbs less heat, which can reduce the waste of heat and save energy.

It can be understood that, the sheet heating unit of the heater 122 is not limited to be totally vertical to the plane where the atomizing surface 1211 is located. In an embodiment, an angle may be formed, that is, the sheet heating unit of the heater 122 may be substantially vertical to the plane where the atomizing surface 1211 is located. In an embodiment, the angle between the width direction of the sheet heating unit and a normal of the plane is within 20 degrees.

It can also be understood that, the sheet heating unit is not limited to the embodiment in which the sheet heating unit as a whole one is substantially vertical to the plane where the atomizing surface 1211 is located; some beneficial effects disclosed in the present disclosure can be achieved if a part of the sheet heating unit of the heater 122 is vertical to the atomizing surface 1211. In an embodiment, at least up to a half of the sheet heating unit can be substantially vertical to the plane.

It can be understood that, in some embodiments, if the moving directions of the e-liquid and/or the smoke in the porous body 121 are not vertical to the plane where the atomizing surface 1211 is located, the arrangement of the sheet heating unit of the heater 122 can be adjusted accordingly such that the sheet heating unit, in the width direction, is parallel to or follow the moving directions of the e-liquid and/or the smoke in the porous body 121 as much as possible.

In some embodiments, the sheet heating unit of the heater 122 can be distributed as evenly as possible around the atomizing surface 1211 in the porous body 121, such that the heat can be distributed more evenly. In some embodiments, the sheet heating unit of the heater 122 can be S-shaped in the length direction; the sheet heating unit includes a certain number of parallel evenly-spaced flat parts 1221 and a certain number of bending sections 1222 connecting the flat parts 1221 together. Correspondingly, the receiving groove 1210 is also S-shaped and a size of the receiving groove 1210 is adaptive to that of the sheet heating unit of the heater 122, thus, the sheet heating unit of the heater 22 can be well received in the receiving groove 1210 and in tight contact with the sheet heating unit of the heater 22. It can be understood that the sheet heating unit of the heater 122 is not limited to be designed to S-shaped, in other embodiments, the sheet heating unit of the heater can be in the shape of strip, tape and wave, etc. In addition, in other embodiments, two or more than two sheet heating units of the heater 122 can be arranged on the porous body 121.

Figure 4:
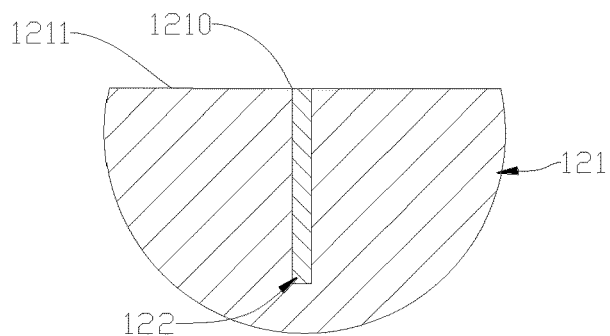
FIG. 4 is a partly enlarged view of a part A of the heating assembly of FIG. 3 in accordance with an embodiment of the present disclosure.

As shown in FIG. 4, in some embodiments, the width of the sheet heating unit of the heater 122 is equal to the depth of the receiving groove 1210. A top surface of the sheet heating unit of the heater 122 is flush with the atomizing surface 1211 when the sheet heating unit of the heater 122 is received in the receiving groove 1210 along the width direction, namely, the plane where the sheet heating unit is located is parallel to the atomizing surface 1211. Because of the exposed top surface (an upper surface defined by the length and thickness) of the sheet heating unit of the heater 122, the heating assembly 12 can more rapidly atomize the e-liquid near the top surface, thus, smoke can be generated rapidly and the heating assembly 12 can be made conveniently.

In some embodiments, a thermal conductivity of the porous body 121 is even along the direction from the liquid-absorbing surface 1212 to the atomizing surface 1211. In other embodiments, the thermal conductivity of the porous body 121 gradually increases along the direction from the liquid-absorbing surface 1212 towards the atomizing surface 1211. As a result, the e-liquid is atomized more rapidly as getting closer to the atomizing surface 1211, thus, the movement of the e-liquid towards the atomizing surface 1211 is accelerated to improve the atomized efficiency.

In addition, the sheet heating unit of the heater 122 is embedded in the porous body 121 along the width direction and a contact area between the sheet heating unit of the heater 122 and the porous body 121 is large, thus, the thermal efficiency is high and the combination is firm and uneasy to shed off. Besides, with such configuration, the sheet heating unit of the heater 122 can be made as thin as possible, and the exposed part of the sheet heating unit of the heater 122 is relatively narrow, which therefore can greatly reduce dry burning on the exposed part of the sheet heating unit of the heater 122.

Figure 5:
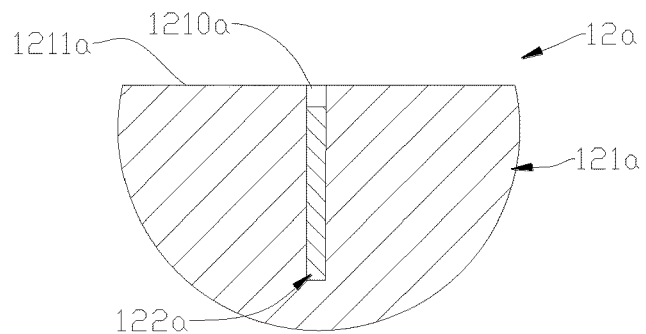
FIG. 5 is a partly enlarged view of a part A of the heating assembly of FIG. 1 in a first alternative solution.

In FIG. 5, a heating assembly 12a in some embodiments is shown. The heating assembly 12a is an alternative solution for the heating assembly 12 mentioned above, and the difference therebetween lies in that a width of a sheet heating unit of a heater 122a of the heating assembly 12a is smaller than a depth of a receiving groove 1210a of the heating assembly 12a, as a result, when the sheet heating unit of the heater 122a is received in the receiving groove 1210a along the width direction, a top surface of the sheet heating unit is lower than an atomizing surface 1211a. Thus, e-liquid may accumulate in a slot channel between the top surface and the atomizing surface 1211a, avoiding the exposure of the top surface and further reducing the dry burning of the heater 122a.

Figure 6:
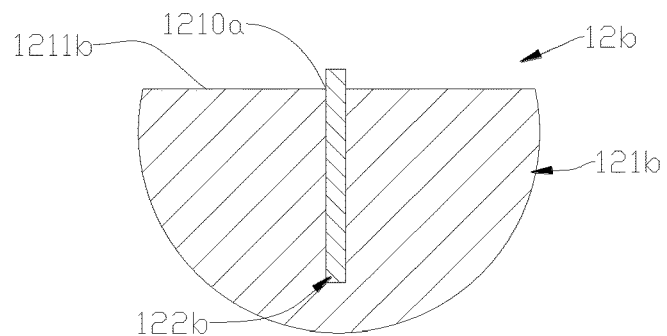
FIG. 6 is a partly enlarged view of a part A of the heating assembly of FIG. 1 in a second alternative solution.

In FIG. 6, a heating assembly 12b in some embodiments is shown. The heating assembly 12b is an alternative solution for the heating assembly 12 mentioned above, and the difference therebetween lies in that a width of a sheet heating unit of a heater 122b is larger than a depth of a receiving groove 1210b, as a result, when the sheet heating unit of the heater 122b is received in the receiving groove 1210b along the width direction, a top surface of the sheet heating unit is higher than an atomizing surface 1211b. Thus, multiple atomization temperatures can be provided to realize various flavour to meet the needs of different customers.

Figure 7:
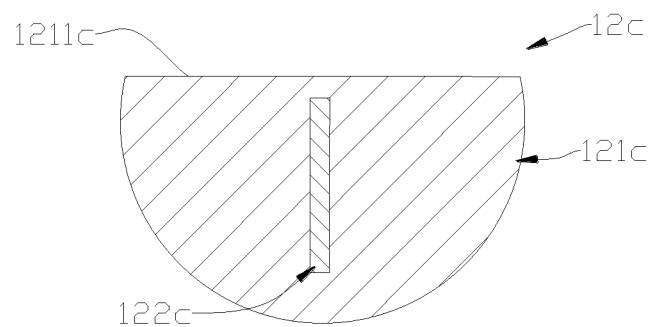
FIG. 7 is a partly enlarged view of a part A of the heating assembly of FIG. 1 in a third alternative solution.

In FIG. 7, a heating assembly 12c in some embodiments is shown. The heating assembly 12c is an alternative solution for the heating assembly 12 above mentioned, and the difference therebetween lies in that a sheet heating unit of a heater 122c is vertical to an atomizing surface 1211c in the width direction and is totally embedded into a porous body 121c. Thus, the dry burning of the heater 122c can be avoided.

Figure 8:
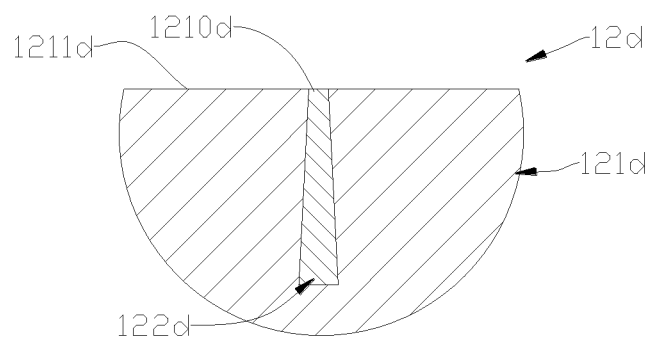
FIG. 8 is a partly enlarged view of a part A of the heating assembly of FIG. 1 in a fourth alternative solution.

In FIG. 8, a heating assembly 12d in some embodiments is shown. A width of a sheet heating unit of a heater 122d of the heating assembly 12d is equal to a depth of a receiving groove 1210d; when the sheet heating unit of the heater 122d is received in the receiving groove 1210d in the width direction, a top surface of the sheet heating unit is flush with an atomizing surface 1211d. As an alternative solution for the heating assembly 12 mentioned above, the difference between the heating assemblies 12d and 12 lies in that a thickness of the sheet heating unit of the heater 122d gradually increases along a depth direction of the receiving groove 1210d, as a result, the resistance of the sheet heating unit of the heater 122d gradually decreases along the depth direction of the receiving groove 1210d.

Figure 9:
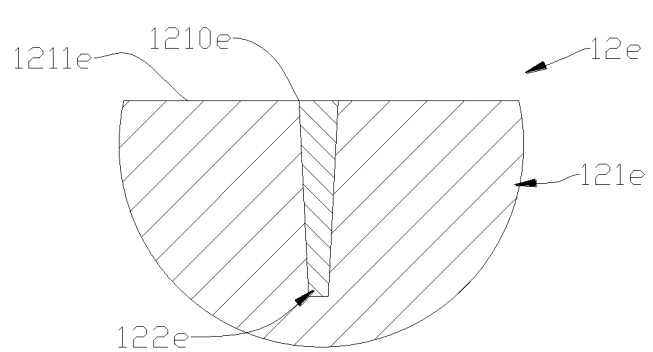
FIG. 9 is a partly enlarged view of a part A of the heating assembly of FIG. 1 in a fifth alternative solution.

In FIG. 9, a heating assembly 12e in some embodiments is shown. A width of a sheet heating unit of a heater 122e is equal to a depth of a receiving groove 1210e; when the sheet heating unit of the heater 122e is received in the receiving groove 1210e in the width direction, a top surface of the sheet heating unit is flush with an atomizing surface 1211e. As an alternative solution for the heating assembly 12 mentioned above, the difference between the heating assemblies 12e and 12 lies in that a thickness of the sheet heating unit of the heater 122e gradually decreases along a depth direction of the receiving groove 1210e, as a result, the resistance of the sheet heating unit of the heater 122e gradually increases along the depth direction of the receiving groove 1210e.

Figure 10:
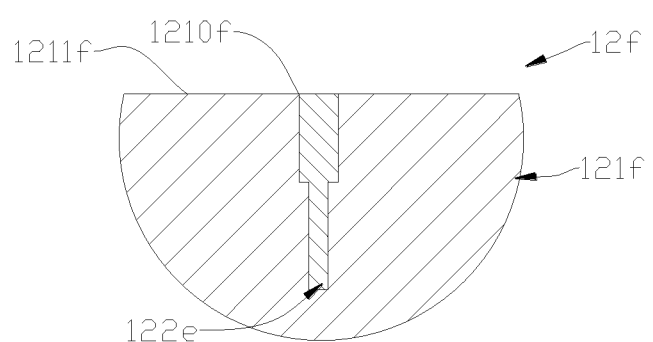
FIG. 10 is a partly enlarged view of a part A of the heating assembly of FIG. 1 in a sixth alternative solution.

In FIG. 10, a heating assembly 12f in some embodiments is shown. A width of a sheet heating unit of a heater 122f is equal to a depth of a receiving groove 1210f; when the sheet heating unit of the heater 122f is received in the receiving groove 1210f in the width direction, a top surface of the sheet heating unit is flush with an atomizing surface 1211f. As an alternative solution for the heating assembly 12 mentioned above, the difference between the heating assemblies 12f and 12 lies in that, a thickness of a part of the sheet heating unit of the heater 122f which is close to an atomizing surface 1211f is larger than that of a part of the sheet heating unit of the heater 122f which is away from the atomizing surface 1211f. Namely, the sheet heating unit of the heater 122f has a stepped thickness, as a result, a resistance of the part of the sheet heating unit of the heater 122f which is close to the atomizing surface 1211f is larger than the resistance of the part of the sheet heating unit of the heater 122f which is away from the atomizing surface 1211f.

Figure 11:
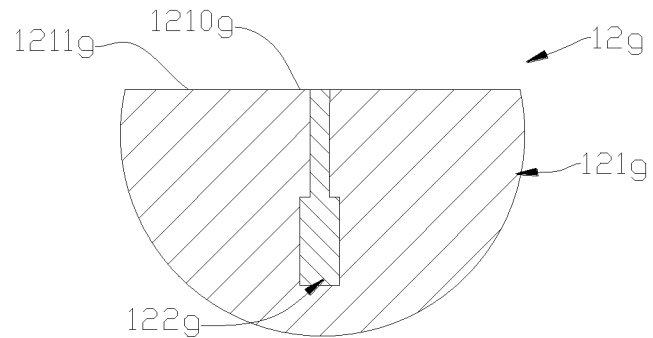
FIG. 11 is a partly enlarged view of a part A of the heating assembly of FIG. 1 in a seventh alternative solution.

In FIG. 11, a heating assembly 12g in some embodiments is shown. A width of a sheet heating unit of a heater 122g is equal to a depth of a receiving groove 1210g; when the sheet heating unit of the heater 122g is received in the receiving groove 1210g in the width direction, a top surface of the sheet heating unit is flush with an atomizing surface 1211g. As an alternative solution for the heating assembly 12 mentioned above, the difference between the heating assemblies 12g and 12 lies in that a thickness of a part of the sheet heating unit of the heater 122g which is close to the atomizing surface 1211g is smaller than a thickness of a part of the sheet heating unit of the heater 122g which is away from the atomizing surface 1211g, as a result, a resistance of the part of the sheet heating unit of the heater 122g which is close to the atomizing surface 1211g is smaller than the resistance of the part of the sheet heating unit of the heater 122g which is away from the atomizing surface 1211g.

Figure 12:
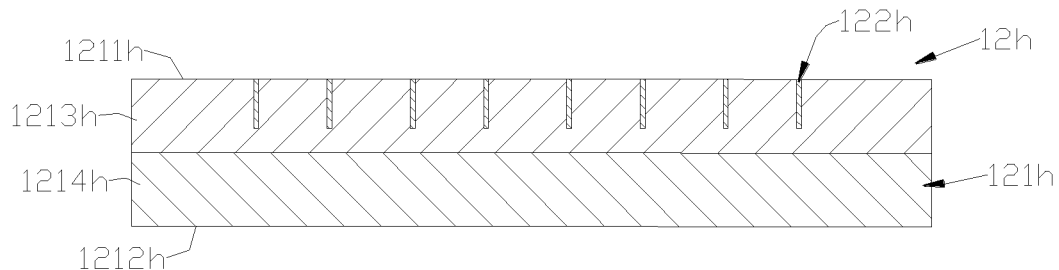
FIG. 12 is a longitudinal cross-sectional view of the heating assembly of FIG. 1 in an eighth alternative solution.

In FIG. 12, a heating assembly 12h in some embodiments is shown. A width of a sheet heating unit of a heater 122h is equal to a depth of a receiving groove 1210h; when the sheet heating unit of the heater 122h is received in the receiving groove 1210h in the width direction, a top surface of the sheet heating unit is flush with an atomizing surface 1211h. As an alternative solution for the heating assembly 12 mentioned above, the difference between the heating assemblies 12f and 12 lies in that, a porous body 121h includes a first layer 1213h which is close to the atomizing surface 1211h and a second layer 1214h which is away from the atomizing surface 1211h, and a thermal conductivity of the first layer 1213h is larger than that of the second layer 1214h, thus, the heat in the part of the sheet heating unit which is close to the atomizing surface 1211h can be transferred faster and thus optimizes the atomized efficiency.

Figure 13:
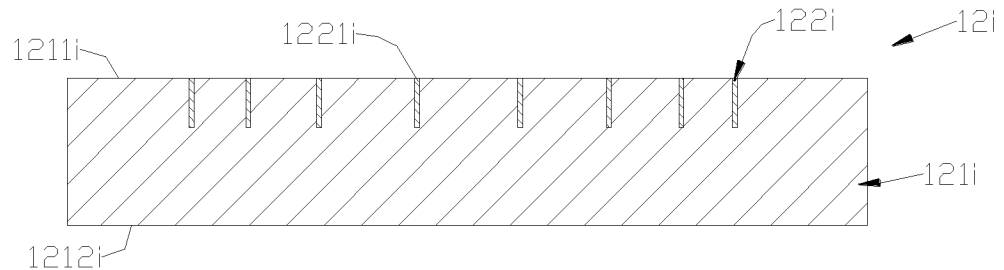
FIG. 13 is a longitudinal cross-sectional view of the heating assembly of FIG. 1 in a ninth alternative solution.

In FIG. 13, a heating assembly 12i in some embodiments is shown. A width of a sheet heating unit of a heater 122i is equal to a depth of a receiving groove 1210i; when the sheet heating unit of the heater 122i is received in the receiving groove 1210i in the width direction, a top surface of the sheet heating unit is flush with an atomizing surface 1211i.

As an alternative solution for the heating assembly 12 mentioned above, the difference between the heating assemblies 12$i$ and 12 lies in that, a density of flat parts 1221$i$ of the heater 122$i$ located in the middle of a plane which is parallel to the atomizing surface 1211$i$ is smaller than that of the flat parts 1221$i$ located in other areas of the plane, which therefore allows for even heating of the heater 122$i$. It can be understood that in some embodiments, the density of the flat parts 1221$i$ located in the middle of the plane can be greater than that of the flat parts 1221$i$ located in other areas of the plane.

Figure 14:
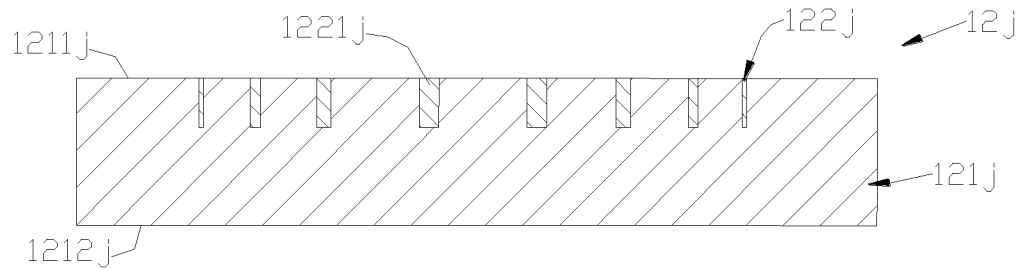
FIG. 14 is a longitudinal cross-sectional view of the heating assembly of FIG. 1 in a tenth alternative solution.

In FIG. 14, a heating assembly 12$j$ in some embodiments is shown. A width of a sheet heating unit of a heater 122$j$ is equal to a depth of a receiving groove 1210$j$; when the sheet heating unit of the heater 122$j$ is received in the receiving groove 1210$j$ in the width direction, a top surface of the sheet heating unit is flush with an atomizing surface 1211$j$. As an alternative solution for the heating assembly 12 mentioned above, the difference between the heating assemblies 12$j$ and 12 lies in that, thicknesses of flat parts 1221$j$ of the heater 122$j$ located in the middle of a plane which is parallel to an atomizing surface 1211$j$ are respectively greater than the thicknesses of the flat parts 1221$j$ located in other areas of the plane.

Figure 15:
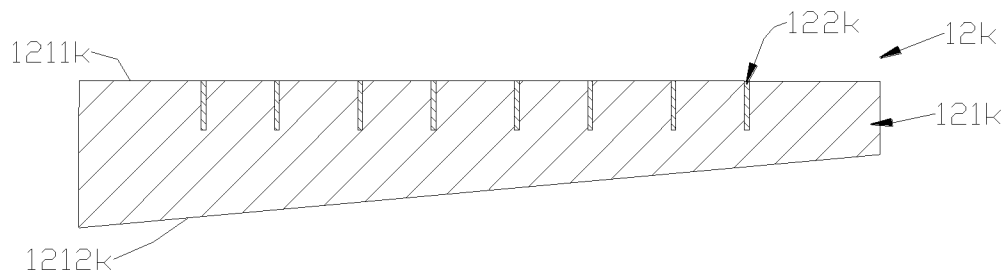
FIG. 15 is a longitudinal cross-sectional view of the heating assembly of FIG. 1 in an eleventh alternative solution.

In FIG. 15, a heating assembly 12$k$ in some embodiments is shown. A width of a sheet heating unit of a heater 122$k$ is equal to a depth of a receiving groove 1210$k$. When the sheet heating unit of the heater 122$k$ is received in the receiving groove 1210$k$ in the width direction, a top surface of the sheet heating unit is flush with an atomizing surface 1211$k$. As an alternative solution for the heating assembly 12 mentioned above, the difference between the heating assemblies 12$k$ and 12 lies in that, a liquid-absorbing surface 1212$k$ is not parallel to the atomizing surface 1211$k$, as a result, a porous body 121$k$ is in the shape of a trapezoid.

Figure 16:
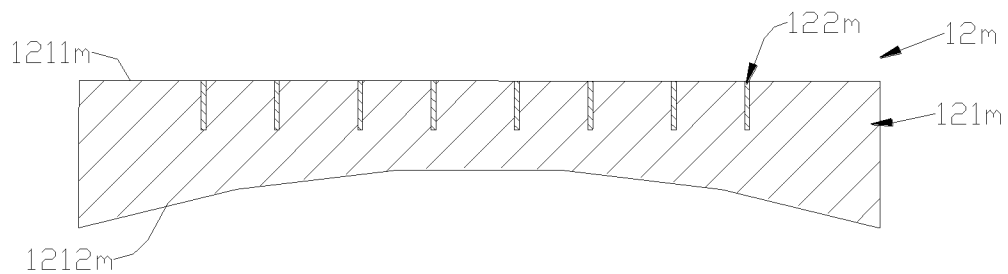
FIG. 16 is a longitudinal cross-sectional view of the heating assembly of FIG. 1 in a twelfth alternative solution.

In FIG. 16, a heating assembly 12$m$ in some embodiments is shown. A width of a sheet heating unit of a heater 122$m$ is equal to a depth of a receiving groove 1210$m$; when the sheet heating unit of the heater 122$m$ is received in the receiving groove 1210$m$ in the width direction, a top surface of the sheet heating unit is flush with an atomizing surface 1211$m$. As an alternative solution for the heating assembly 12 mentioned above, the difference between the heating assemblies 12$m$ and 12 lies in that, a liquid-absorbing surface 1212$m$ is a concave arc surface.

Figure 17:
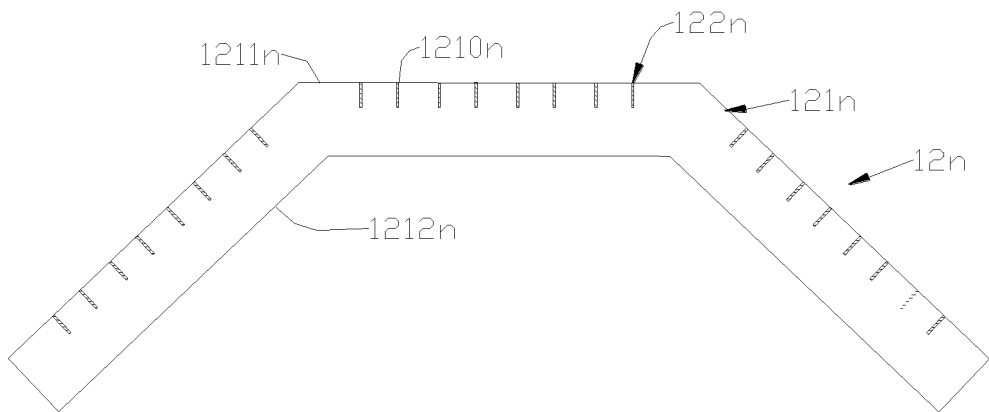
FIG. 17 is a longitudinal cross-sectional view of the heating assembly of FIG. 1 in a thirteenth alternative solution.

In FIG. 17, a heating assembly 12$n$ in some embodiments is shown. The heating assembly 12$n$ is an alternative solution for a heating assembly 12 mentioned above, and the difference therebetween lies in that, a porous body 121$n$ of the heating assembly 12$n$ includes three atomizing surfaces 1211$n$ and three liquid-absorbing surfaces 1212$n$. Each atomizing surface 1211$n$ corresponds to a sheet heating unit of a heater 122$n$, and a width of each atomizing surface 1211$n$ is equal to a depth of a corresponding receiving groove 1210$n$; when the sheet heating unit of the heater 122$n$ is received in the receiving groove 1210$n$ in the width direction, a top surface of the sheet heating unit is flush with the atomizing surface 1211$n$. Each liquid-absorbing surface 1212$n$ is parallel to the corresponding atomizing surface 1211$n$. It can be understood that the number of the atomizing surface 1211$n$ can be two or more than three.

Figure 18:
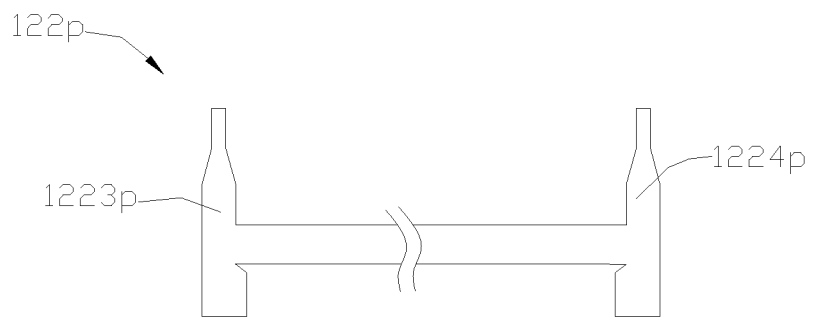
FIG. 18 is a schematic view of a heater of the heating assembly of FIG. 1 in a first alternative solution.

In FIG. 18, a sheet heating unit of a heater 122$p$ in some embodiments is shown. The heater 122$p$ is an alternative solution for the heater 122 of the heating assembly 12 mentioned above, and the difference therebetween lies in that, the heater 122$p$ includes an elongated sheet heating unit in the middle and two electrical connecting units 1223$p$ and 1224$p$ respectively connected to two ends of the elongated sheet heating unit. As shown in FIG. 18, instead of being bent into a specific shape, the elongated sheet heating unit is in the shape of a strip. In some embodiments, the sheet heating unit is integrated with the two electrical connecting units 1223$p$ and 1224$p$, and lower parts of the two electrical connecting units 1223$p$ and 1224$p$ respectively protrude from a lower edge of the sheet heating unit. Thus, when the sheet heating unit of the heater 122$p$ is inserted into a porous body, the electrical connecting units 1223$p$ and 1224$p$ can be inserted more deeply to engage with the porous body more firmly to avoid the loosening of the sheet heating unit caused by pulling of lead wires. Upper parts of the two electrical connecting units 1223$p$ and 1224$p$ respectively protrude from an upper edge of the sheet heating unit to act as electrical lead wires.

Figure 19:
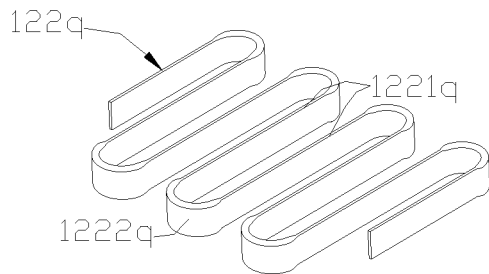
FIG. 19 is a schematic view of the heater of the heating assembly of FIG. 1 in a second alternative solution.

In FIG. 19, a sheet heating unit of a heater 122$q$ in some embodiments is shown. The sheet heating unit of the heater 122$q$ is shaped as a "S" strip, which includes a certain number of parallel flat parts 1221$q$ and a certain number of bending sections 1222$q$ which connect the flat parts 1221$q$ together. The sheet heating unit of the heater 122$q$ is an alternative solution for the sheet heating unit of the heater 122 of the heating assembly 12, and the difference therebetween lies in that, a thickness of the bending section 1222$q$ is greater than a thickness of the flat part 1221$q$, which reduces a resistance of the bending section 1222$q$ and reduces the accumulated heat produced from the bending section 1222$q$. In some embodiments, the bending section 1222$q$ can be widened to reduce the resistance of the bending section 1222$q$. It can be understood that the solution is not limited to the sheet heating unit; in other embodiments, a heating coil and a coating sheet heating unit are also applicable. In an embodiment, when the heating coil has the flat part and the bending section, the bending section can be designed to be larger, while for the coating heaters, the coat on the bending section can be thicker or wider.

Figure 20:
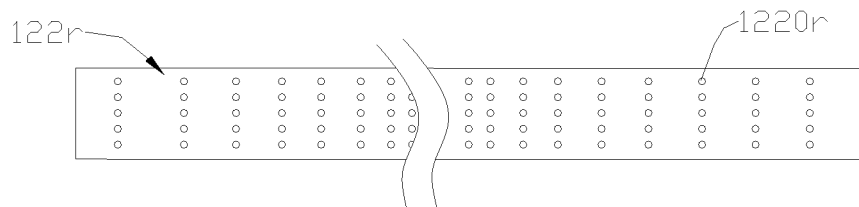
FIG. 20 is a schematic view of the heater of the heating assembly of FIG. 1 in a third alternative solution.

In FIG. 20, a sheet heating unit of a heater 122$r$ in some embodiments is shown. The sheet heating unit of the heater 122$r$ is an alternative solution for the sheet heating unit of the heater 122, and the difference therebetween lies in that, the sheet heating unit of the heater 122$r$ defines multiple through holes 1220$r$ running through the thickness direction of the sheet heating unit. In the length direction of the sheet heating unit of the heater 122$r$, a density of the through holes in the middle of the sheet heating unit is greater than that of the through holes in two ends of the sheet heating unit. Thus, in the length direction of the sheet heating unit, the resistance of the sheet heating unit in the middle is greater than the resistances of the sheet heating unit in both two ends, which is capable of meeting requirements of the specific heating assembly and allows the distribution of the heat in the porous body to meet the specific needs.

Figure 21:
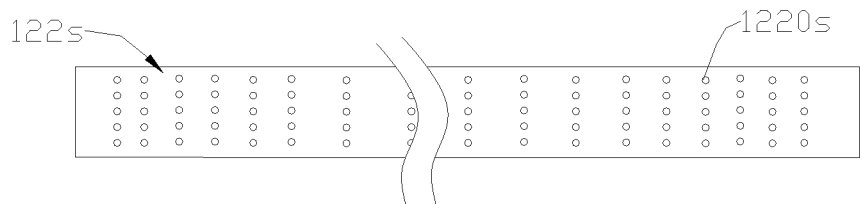
FIG. 21 is a schematic view of the heater of the heating assembly of FIG. 1 in a fourth alternative solution.

In FIG. 21, a sheet heating unit of a heater 122$s$ in some embodiments is shown. The sheet heating unit of the heater 122$s$ is an alternative solution for the sheet heating unit of the heater 122, and the difference therebetween lies in that, the sheet heating unit of the heater defines multiple through holes 1220$s$ running through the thickness direction thereof. In the length direction of the sheet heating unit, a density of the through holes in the middle is less than that of the through holes in both ends of the sheet heating unit. Thus, in the length direction of the sheet heating unit, the resistance of the sheet heating unit in the middle is less than that of the sheet heating unit in both ends to meet the requirements of the specific heating assembly.

Figure 22:
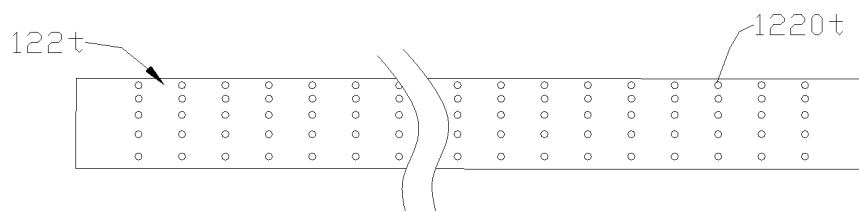
FIG. 22 is a schematic view of the heater of the heating assembly of FIG. 1 in a fifth alternative solution.

In FIG. 22, a sheet heating unit of a heater 122t in some embodiments is shown. As an alternative solution for the sheet heating unit of the heater 122, the difference between the heaters 122 and 122t lies in that, the sheet heating unit of the heater 122t defines multiple through holes 1220t running through the thickness direction thereof, and the density of the through holes 1220t gradually changes (e.g., gradually increases or gradually decreases) or steppedly changes in the width direction of the sheet heating unit. Thus, the resistance of the sheet heating unit of the heater 122t gradually changes or steppedly changes in the width direction of the sheet heating unit to meet the requirements of different heating assemblies.

Figure 23:
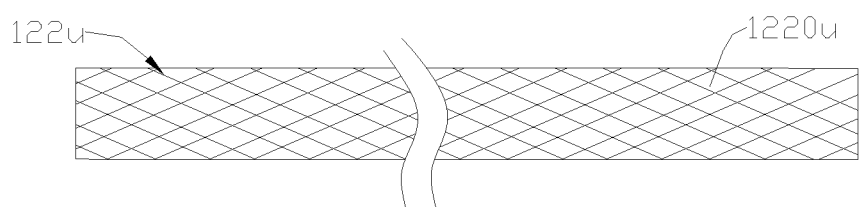
FIG. 23 is a schematic view of the heater of the heating assembly of FIG. 1 in a sixth alternative solution.

In FIG. 23, a sheet heating unit of a heater 122u in some embodiments is shown. As an alternative solution for the sheet heating unit of the heater 122, the difference between the heaters 122u and 122 lies in that, the sheet heating unit of the heater 122u is a heating net with lots of meshes 1220u, and the distribution of the meshes 1220u in the length direction of the sheet heating unit can be one of the followings. In a first type, the meshes is evenly distributed, which makes the resistance be evenly distributed in the length direction of the sheet heating unit; in a second type, the density of the meshes in the middle of the sheet heating unit is less than that of the meshes in two ends of the sheet heating unit, and the density of the meshes gradually changes or steppedly changes; in a third type, the density of the meshes in the middle of the sheet heating unit is greater than that of the meshes in two ends of the sheet heating unit, and the density of the meshes gradually changes or steppedly changes. In the width direction of the sheet heating unit of the heater 122u, the meshes 1220u can be evenly distributed; or the meshes in one end are denser than the meshes in the other end of the sheet heating unit, and the density of the meshes gradually changes or steppedly changes.

Figure 24:
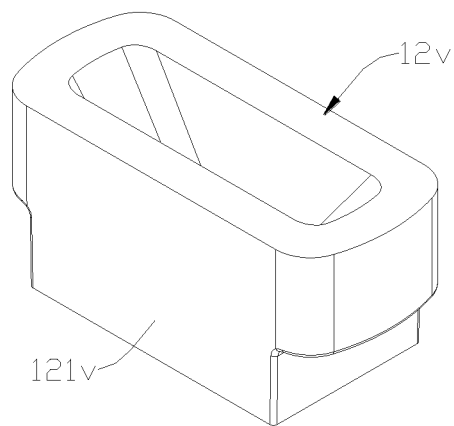
FIG. 24 is a three-dimension assembled view of the heating assembly of FIG. 1 in a fourteenth alternative solution.
Figure 25:
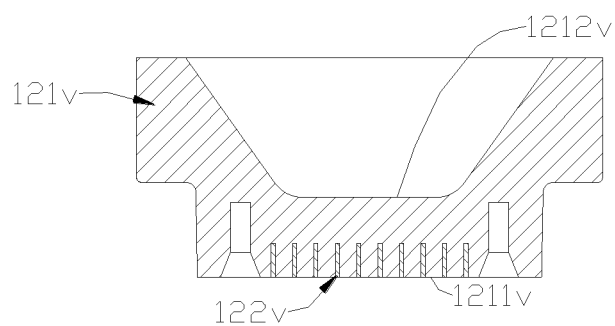
FIG. 25 is a longitudinal cross-sectional view of the heating assembly of FIG. 24 in accordance with an embodiment of the present disclosure.

In FIG. 24 and FIG. 25, a heating assembly 12v in some embodiments is shown. The heating assembly 12v includes a porous body 121v and a sheet heating unit of a heater 122v arranged in the porous body 121v. As an alternative solution for the heating assembly 12, the difference between the heating assemblies 12v and 12 lies in that, a liquid-absorbing surface 120v of the porous body 121v of the heating assembly 12v is recessed to form a groove 120v, which makes the whole porous body 121v be in the shape of a bowl. An inner surface of a bottom wall of the porous body 121v forms a liquid-absorbing surface 1212v, while an outer surface of the bottom wall of the porous body 121v forms an atomizing surface 1211v. The sheet heating unit of the heater 122v is embedded on the atomizing surface 1211v. Since the porous body 121v is in the shape of a bowl, the whole porous body 121v is high enough to facilitate the installation of the heating assembly 12v and the arrangement of a seal cartridge 13. Besides, the distance from the liquid-absorbing surface 1212v to the atomizing surface 1211v is close enough for convenient installation and improving the atomized effect. The heater 122v can be any heater mentioned above.

Figure 26:
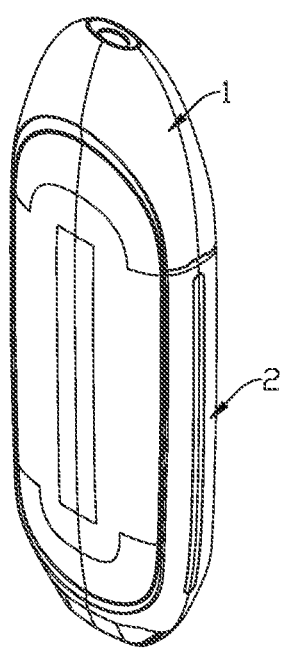
FIG. 26 is a three-dimension assembled view of an electronic cigarette with the heating assembly of FIG. 24 in accordance with an embodiment of the present disclosure.
Figure 27:
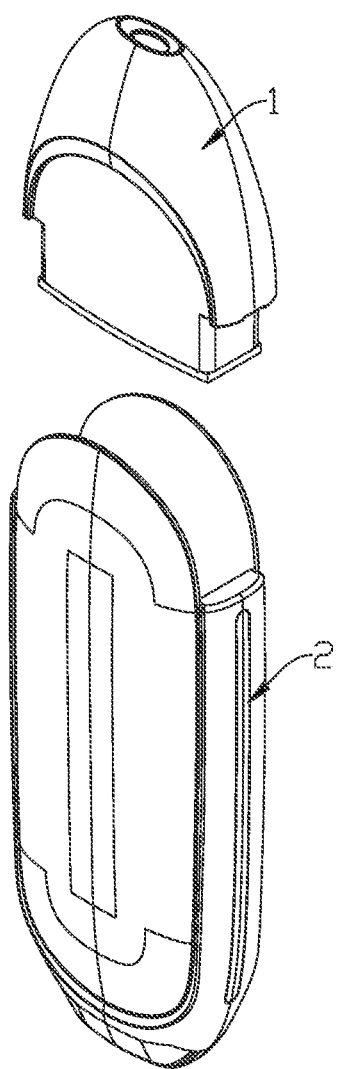
FIG. 27 is a three-dimension exploded view of the electronic cigarette of FIG. 26 in accordance with an embodiment of the present disclosure.

In FIG. 26 and FIG. 27, an electronic cigarette in some embodiments is shown. The heating assembly 12v shown in FIG. 24 and FIG. 25 is adopted in the electronic cigarette. It can be understood that any heating assembly mentioned above is adaptable to the electronic cigarette. In some embodiments, the electronic cigarette can be flat, including an atomizer 1 and a battery assembly 2 detachably connected to the atomizer 1. The atomizer 1 is used for containing e-liquid to generate the smoke. The battery assembly 2 is configured for supplying electricity for the atomizer 1. As shown, a lower part of the atomizer 1 is inserted into an upper part of the battery assembly 2; in some embodiments, the atomizer 1 and the battery assembly 2 can be coupled together through magnet.

Figure 28:
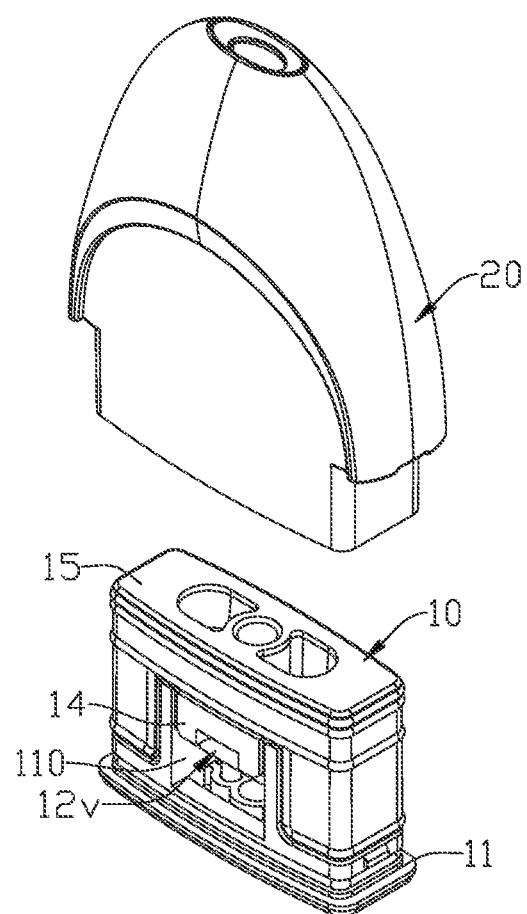
FIG. 28 is a three-dimension exploded view of an atomizer of the electronic cigarette of FIG. 26 in accordance with an embodiment of the present disclosure.
Figure 29:
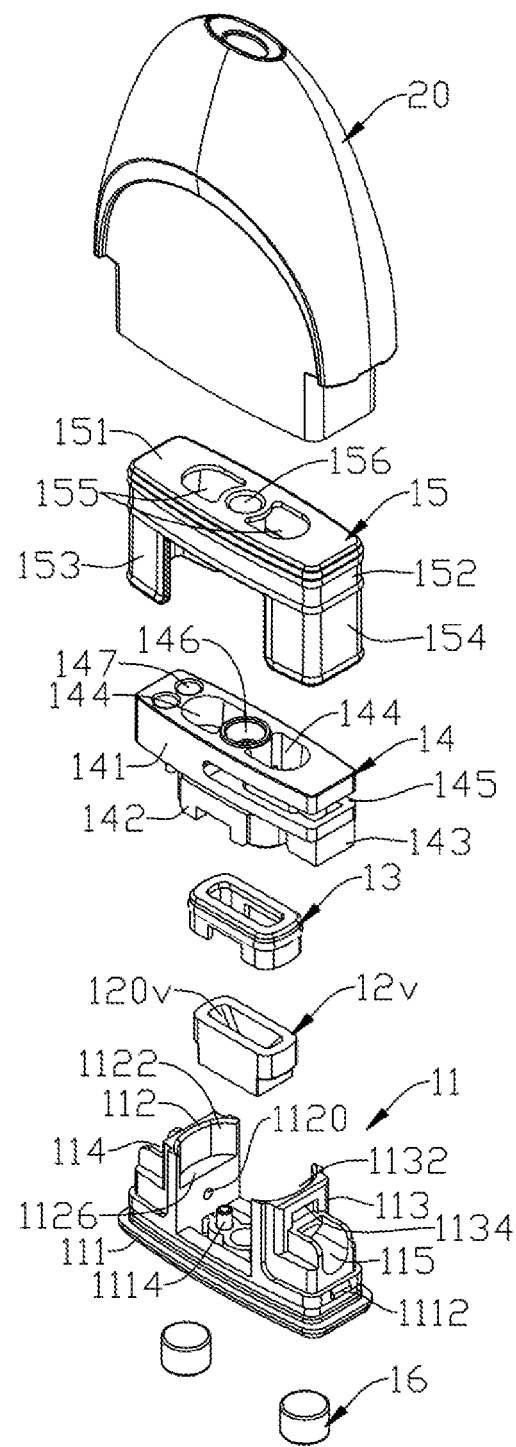
FIG. 29 is a further three-dimension exploded view of the atomizer of the electronic cigarette of FIG. 26 in accordance with an embodiment of the present disclosure.
Figure 30:
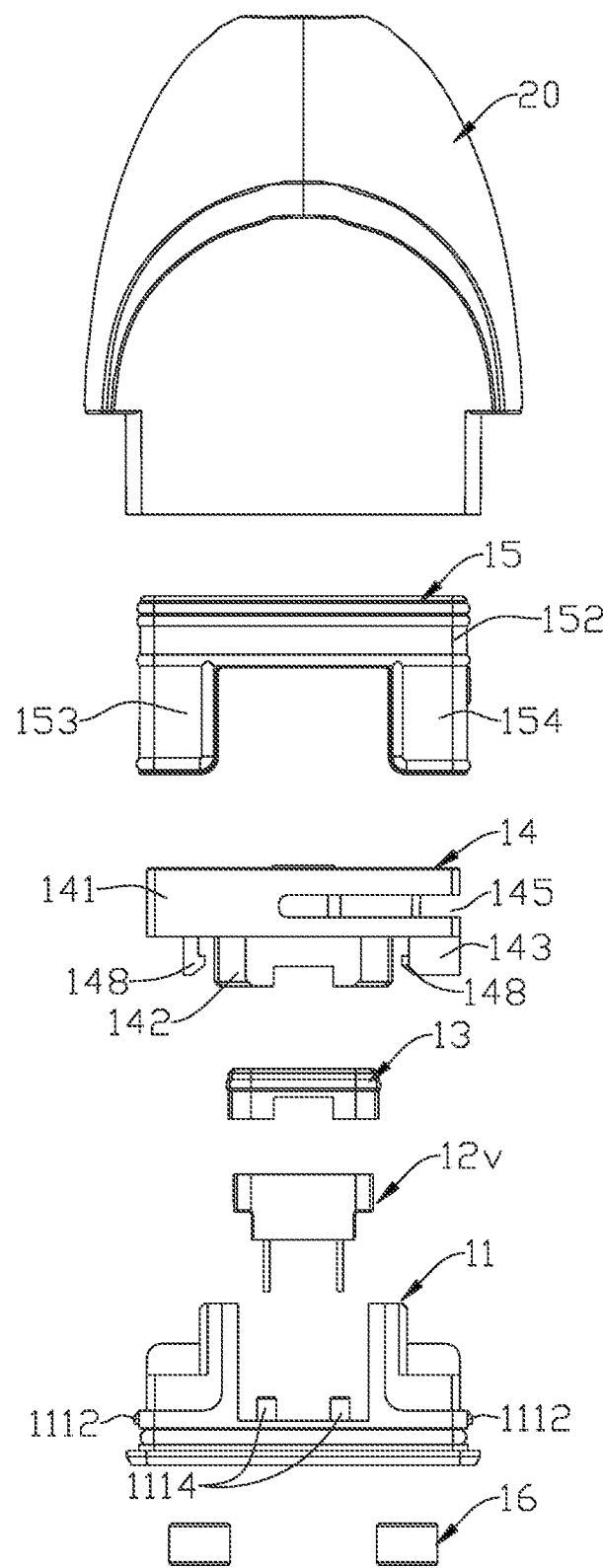
FIG. 30 is a two-dimension exploded view of the atomizer of the electronic cigarette of FIG. 26 in accordance with an embodiment of the present disclosure.
Figure 31:
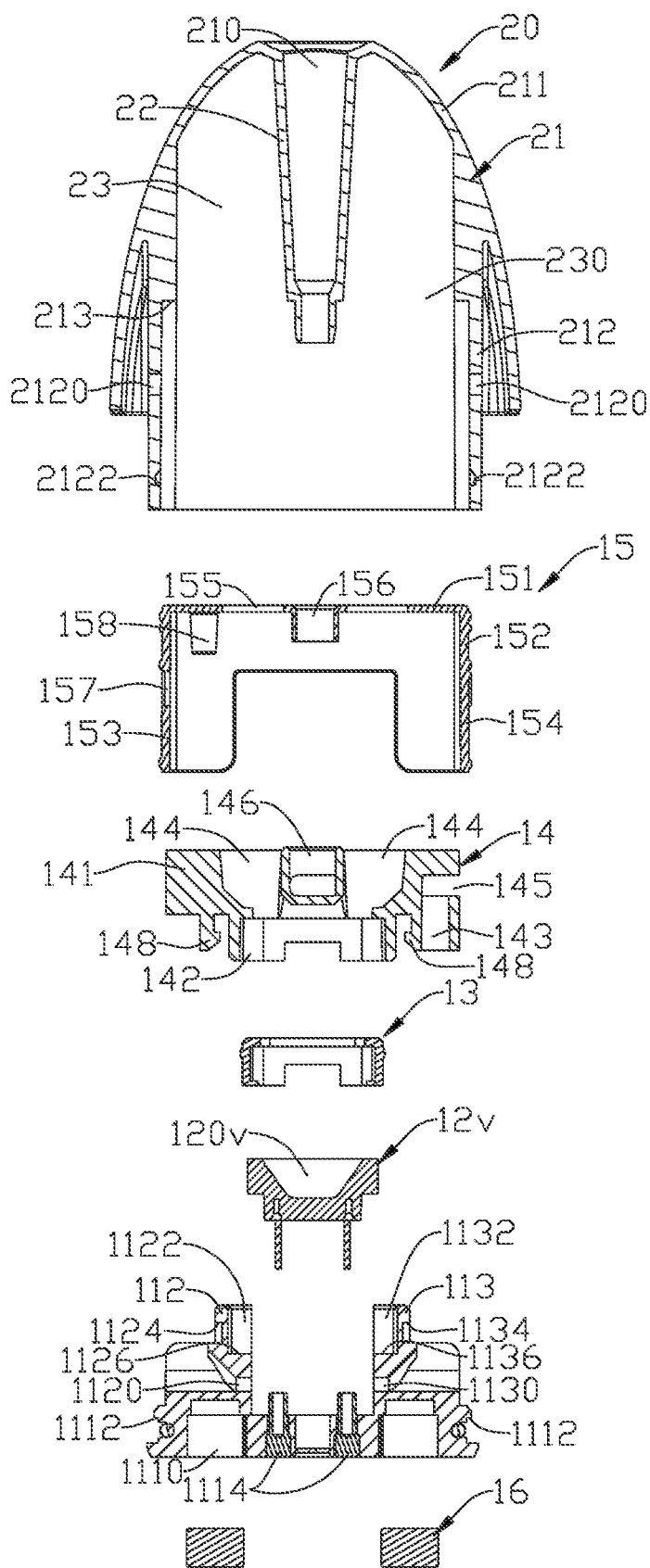
FIG. 31 is a general cross-sectional exploded view of the atomizer of the electronic cigarette of FIG. 26 in accordance with an embodiment of the present disclosure.

As shown in FIG. 28, in some embodiments, the atomizer 1 can include an atomization assembly 10 and a liquid reservoir 20 sleeved on the atomization assembly 10. The atomization assembly 10 can be used for heating and atomizing the e-liquid, while the liquid reservoir 20 is used to store the e-liquid for the atomization assembly 10.

As shown from FIG. 29 to FIG. 32, the atomization assembly 10 includes a lower holder 11, the heating assembly 12v arranged on the lower holder 11, a seal cartridge 13 sleeved on the heating assembly 12v, an upper holder 14 installed on the lower holder 11 and abutting against the seal cartridge 13, and a sleeving cover 15 sleeved on the upper holder 14. After the upper holder 14 abuts against the seal cartridge 13, the heating assembly 12v is tightly clamped between the lower holder 11 and the upper holder 14. The seal cartridge 13 can seal the heating assembly 12v and the upper holder 14 to prevent leakage of e-liquid and fasten the heating assembly 12v in the horizontal direction.

In some embodiments, the lower holder 11 includes a base 111, a first supporting arm 112 installed on a top surface of the base 111, and a second supporting arm 113 installed on the top surface of the base 111 and corresponding to the first supporting arm 112. The heating assembly 12v is installed between the first supporting arm 112 and the second supporting arm 113. The atomizing surface 1211v faces the base 111 directly and is spaced from the base at an interval which forms the atomization cavity 110 such that the smoke can mix with the air.

In some embodiments, the base 111 can be a rectangle plate. A bottom side of the base 111 is recessed to form two accommodating grooves 1110 for accommodating two magnetic assemblies 16 which are used to magnetize the atomizer 1 and the battery assembly 2 together. First hooks 1112 are respectively formed on opposite end surfaces of the base 111 to be clamped to the liquid reservoir 20. Two electrodes 1114 electrically connected to the heating assembly 12v can be formed on a bottom of the base 111. The two electrodes 1114 are respectively electrically connected to positive and negative poles the battery assembly 2.

In some embodiments, the first supporting arm 112 and the second supporting arm 113 can be shaped as plates. Inner sides of the first supporting arm 112 and the second supporting arm 113 are respectively recessed to form containing grooves 1122, 1132 for receiving an embedded portion 142 of the upper holder 14. The containing grooves 1122, 1132 are respectively formed in the upper portions of the first supporting arm 112 and the second supporting arm 113. The containing grooves 1122, 1132 respectively form steps 1126, 1136 on the first supporting arm 112 and the second supporting arm 113. Two ends of the heating assembly 12v are respectively held by the steps 1126, 1136. Two clamping portions 1124 and 1134 used for being clamped to the upper holder 14 are respectively arranged on outer sides of top ends of the first supporting arm 112 and the second supporting arm 113. In some embodiments, the first supporting arm 112 and the second supporting arm 113 are symmetrically arranged to facilitate the installation thereof, namely, there is no need to distinguish which supporting arm is the right one and which supporting arm is the left one during the assembly of the supporting arms 112, 113.

In some embodiments, the lower holder 11 can also include a U-shaped intake groove structure 114 and a U-shaped exhaust groove structure 115, which are respectively connected to outer sides of the first supporting arm 112 and the second supporting arm 113 and stretch outwards horizontally. A through hole 1120 communicating the intake groove structure 114 with the atomization cavity 110 is defined in the first supporting arm 112, and a through hole 1120 communicating the exhaust groove structure 115 with the atomization cavity 110 is defined in the second supporting arm 113. The through holes 1120 and 1130 are capable of leading the air into the atomization cavity 110 and taking the smoke in the atomization cavity 110 away. The through holes 1120 and 1130 are respectively located under the containing grooves 1122 and 1132.

In some embodiments, the upper holder 14 can include a main body 141 which is substantially cuboid shaped, an annular embedded portion 142 which extends out of from the middle of a bottom surface of the main body 141, and a second intake channel 143 extending downwards from the right end of the bottom surface of the main body 141. The embedded portion 142 is contained in the containing grooves 1122 and 1132 between the first supporting arm 112 and the second supporting arm 113 of the lower holder 111 and is sleeved on the seal cartridge 13. The upper holder 14 also includes two liquid channels 144, a slot channel 145, and a second exhaust channel 146. The liquid channels 144 extend from the top surface to the bottom surface of the main body 141. The slot channel 145 is formed on a side wall of the main body 141, surrounding the right liquid channel 144 and communicating with the second intake channel 143. The second exhaust channel 146 runs through the middle of the top surface of the upper holder 14 to communicate with the slot channel 145. The left end of the top surface of the upper holder 14 is recessed to define two positioning holes 147, which cooperate with the sleeving cover 15 to play the function of location and fool-proofing. The upper holder 14 also includes a second hook 148 extending downwards to be hooked onto the lower holder 11.

In some embodiments, the sleeving cover 15 can be made of silicone, which can include a top wall 151, a first annular blocking arm 152 which extends downwards from a periphery of the top wall 151, and two second U-shaped blocking arms 153 and 154 which extend downwards from two ends of the first blocking arm 152. Two liquid inlets 155 and a sleeve cover exhaust channel 156 are formed on the top wall 151. The two liquid inlets 155 respectively correspond to the two liquid channels 144 of the upper holder 14. The sleeve cover exhaust channel 156 is inserted into the second exhaust channel 146 and communicates with the second exhaust channel 146. The first blocking arm 152 is used to enclose the side wall of the main body 141 and cover the slot channel 145 on the side wall to form an air-tight annular connecting channel in the upper holder 14. The second blocking arms 153 and 154 respectively cover on the intake groove structure 114 and the exhaust groove structure 115 on the lower holder 11 to respectively form a first air-tight intake channel and a first air-tight exhaust channel cooperating with the first supporting arm 112 and the second supporting arm 113. A first air intake 157 communicating with the external environment is formed on the second blocking arm 153, thus, air can be guided into the first intake channel through the first air intake 157. The first exhaust channel communicates with the second intake channel 143. Two positioning columns 158 extend downwards from the left end of the bottom surface of the top wall 151 of the sleeving cover 15. The two positioning columns 158 respectively cooperate with the two positioning holes 147 in the upper holder 14 so that the first air intake 157 can be precisely located on the left side of the assembly of the upper holder 14 and the lower holder 11 and the first air intake 157 can communicate with the first intake channel to play the function of fool-proofing.

The liquid reservoir 20 includes a shell 21 with an air outlet 210, and an airflow tube 22 arranged in the shell 21 and communicating with the air outlet 210. The shell 21 includes a liquid storage unit 211 and a sleeving portion 212 connected to the liquid storage unit 211. The liquid storage cavity 23 is formed between the liquid storage unit 211 and the airflow tube 22. The liquid storage cavity 23 includes a liquid outlet 230, and the sleeving portion 212 is sleeved on a periphery of the liquid outlet 230 such that the sleeving portion 212 can be tightly sleeved on the atomization assembly 10. A step 213 is formed between an inner surface of the sleeving portion 212 and an inner surface of the liquid storage unit 211. The step 213 abuts against the top surface of the atomization assembly 10. In some embodiments, the sleeving portion 212 is integrated with the liquid storage unit 211. The air outlet 210 can be designed to be a suction nozzle in the shape of a flat trumpet.

The airflow tube 22 extends towards the liquid outlet 230 from the air outlet 210, and a distal end of the airflow tube 22 extends into the sleeving portion 212 and is inserted into the air outlet 210 of the sleeving cover 15, thus, the airflow tube 22 communicates with the second exhaust channel 146. Second air intakes 2120 are formed in the left and right sides of the sleeving portion 212, wherein the left second air intake 2120 communicates with the first air intake 157 in the sleeving cover 15 so as to guide the air outside the shell 21 into the first intake channel which is formed by the sleeving cover 15 and the lower holder 11. In an embodiment, the shell 21 is symmetrically configured for convenient installation. That is because if the shell 21 defines only one second air intake 2120 in one side of the sleeving portion 212, a step to judge whether the second air intake 2120 is on the same side as the first air intake 157 would be required when the shell 21 is being assembled. Clamping slots 2122 are formed in inner walls of the left and right sides of the sleeving portion 212 to respectively cooperate with the first hooks 1112 of the lower holder 11 to fasten the shell 21 and the lower holder 11 conveniently.

The assembly of the atomizer 1 can be performed through following steps:

step a, sleeving the seal cartridge 13 on the heating assembly 12v;

step b, inserting the combination of the seal cartridge 13 and the heating assembly 12v into the embedded portion 142 of the upper holder 14;

step c, covering the upper holder 14 on the lower holder 11 such that the second hook 148 of the heating assembly 12v of the upper holder 14 can be clamped onto the clamping portions 1124 and 1134 of the lower holder 11 and thus the upper holder 14 can be clamped onto the lower holder 11, and electrically connecting electrode leads of the heating assembly 12v to the electrode 1114 on the lower holder 11;

step d, sleeving the sleeving cover 15 on the upper holder 14 to finish the assembling of the atomization assembly 10; and step e, inserting the liquid reservoir 20 with the e-liquid into the sleeving portion 212 such that a top surface of the liquid reservoir 20 abuts against the step 213 to block the liquid outlet 230 of the liquid storage cavity 23, and clamping the first hook 1112 of the lower holder 11 into the clamping slot 2111 of the sleeving portion 212 to finish the convenient and quick assembling of the atomizer 1.

Figure 32:
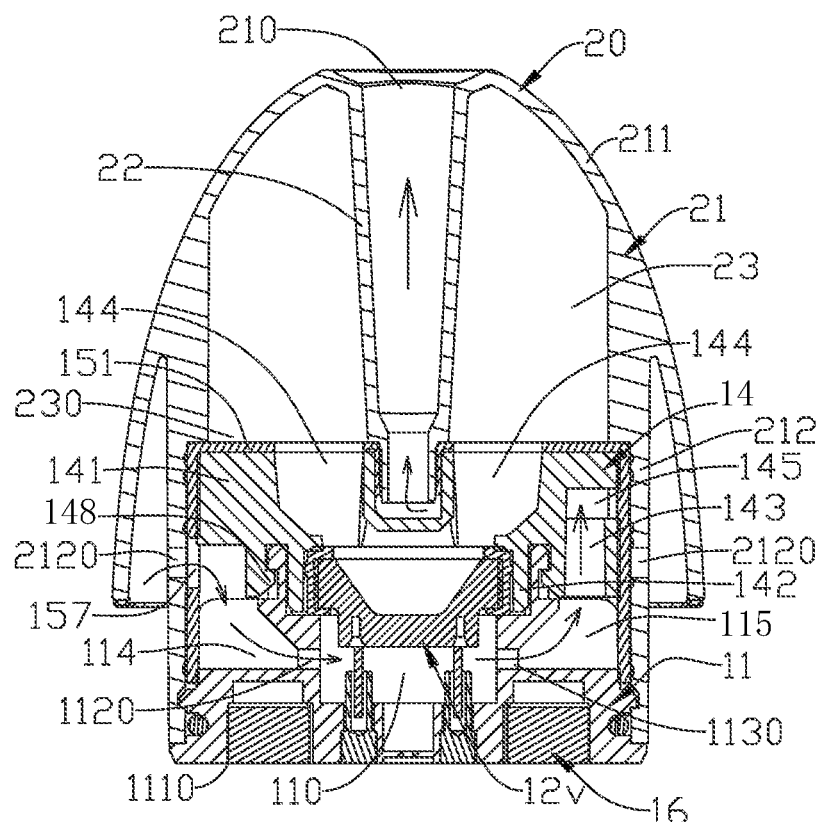
FIG. 32 is a longitudinal cross-sectional assembled view of the atomizer of the electronic cigarette of FIG. 26 in accordance with an embodiment of the present disclosure.

As a result, as the flow path shown by the arrow in FIG. 32, the air at first flows into the first intake channel through the second air intake 2120 and the first air intake 157, and then flows into the atomization cavity 110 to mix with the smoke through the through hole 1120. The mixture of smoke and air flows into the first exhaust channel through the through hole 1130 and then flows into the second intake channel 143. The mixture of smoke and air then sequentially flows into the annular connecting channel, the second exhaust channel 1466, and the airflow tube 22, and finally is exhausted out of the atomizer 1 through the air outlet 210. The e-liquid in the liquid storage cavity 23 flows through the liquid intake 155 of the sleeving cover 15 and the liquid channel 144 of the upper holder 14 in turn, and then flows into the groove 120 of the heating assembly 12v to contact with the liquid-absorbing surface 1212v to realize the delivery of the e-liquid.

In some embodiments, the location of the second air intake 2120 is higher than that of the atomization cavity 110, which can better prevent the leakage of the e-liquid from the second air intake 2120 under normal use. The whole bottom of the airflow tube of the atomizer 1 is substantially U-shaped. The direction of the airflow at the atomization cavity 110 is parallel to the atomizing surface 1211v of the heating assembly 12v, which makes it easier to take away the smoke atomized by the atomizing surface 1211v.

In some embodiments, a groove is formed in the top surface of the porous body 121v of the heating assembly 12v. After the e-liquid flows into the groove, the delivering efficiency of the liquid can be improved. In an embodiment, on the one hand, the groove increases the contact area between the porous body and the e-liquid; on the other hand, the distance between the bottom of the groove and the outer surface of the bottom of the porous body 121v can be very small, which reduces the flow resistance for the e-liquid to reach the outer surface of the bottom of the porous body 121v. Besides, since the seal cartridge 13 is arranged on a liquid delivery side of the heater 122v to seal the e-liquid and prevent the e-liquid from flowing into the atomization cavity 110, the porous body 121v generally has a certain height to allow for the arrangement of the seal cartridge 13 and the rigid demands of the porous body 121v. The groove mentioned above can not only meet the thickness requirement of the porous ceramics, but also meet the needs of the liquid delivering efficiency.

It can be understood that other suitable heating assemblies can be used to replace the heating assembly 12v of the electronic cigarette mentioned above. The heating unit of the heater 122v is not limited to be in the shape of an elongated sheet; in other embodiments, the heating unit of the heater 122v can have other shapes like a strip.

Figure 33:
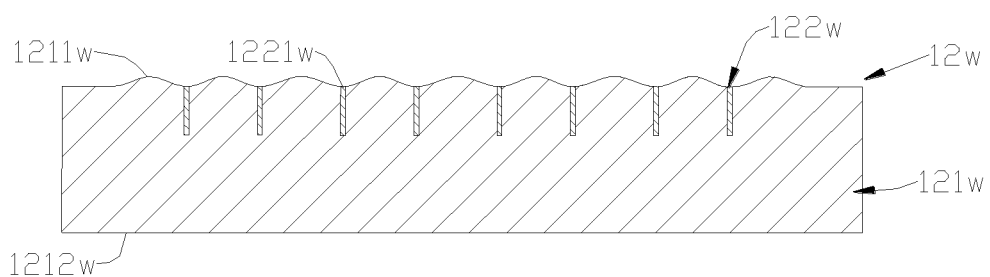
FIG. 33 is a three-dimension schematic view of the heating assembly of FIG. 1 in a fifteenth alternative solution.

In FIG. 33, a heating assembly 12w of in some embodiments is shown. As an alternative solution of the heating assembly 12 mentioned above, the difference between the heating assemblies 12 and 12w lies in that, a porous body 121w of the heating assembly 12w includes a wavy atomizing surface 1211w, and flat parts 1221w of the sheet heating unit of a heater 122w are respectively arranged corresponding to troughs of the wavy atomizing surface 1211w and are vertical to a plane where the wavy atomizing surface 1211w is located, thereby reducing the dry burning of the heating assembly 122w through the e-liquid accumulated on the troughs of the wavy atomizing surface 1211w.

Figure 34:
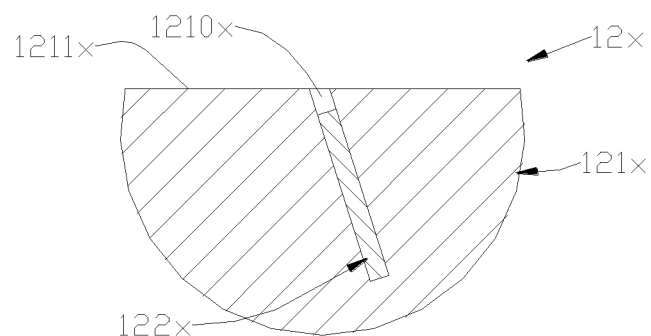
FIG. 34 is a three-dimension schematic view of the heating assembly of FIG. 1 in a sixteenth alternative solution.

In FIG. 34, a heating assembly 12x in some embodiments is shown. A width of the sheet heating unit of a heater 122x of the heating assembly 12x is smaller than a depth of a receiving groove 1210x. Therefore, when the sheet heating unit of the heater 122x is received in the receiving groove 1210x in the width direction, a top surface of the sheet heating unit is lower than an atomizing surface 1211x of the heating assembly 12x. As an alternative solution for the heating assembly 12a mentioned above, the difference between the heating assembly 12a and 12x lies in that, an included angle is formed between the width direction of the sheet heating unit of the heater 122x of the heating assembly 12x and a normal direction of the atomizing surface 1211x. In an embodiment, the angle can be less than 20 degrees.

Figure 35:
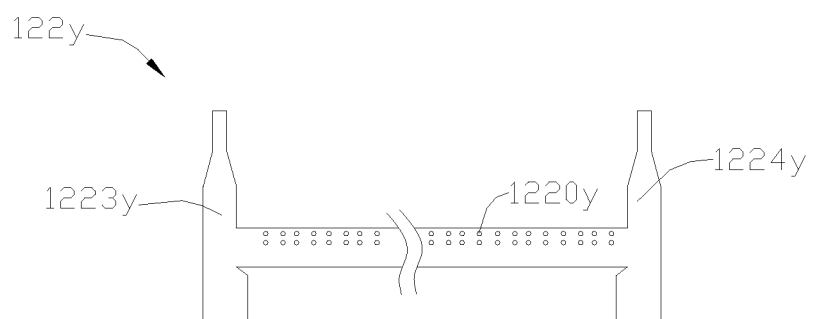
FIG. 35 is a schematic view of the heater of the heating assembly of FIG. 18 in a first alternative solution.

In FIG. 35, a heater 122y in some embodiments is shown. The heater 122y includes a strip-shaped heating unit in the middle and two electrical connection units 1223y and 1224y respectively integrally connected with two ends of the heating unit. As an alternative solution for the heater 122p mentioned above, the difference between the heating heaters 122y and 122p lies in that, many through holes or blind holes 1220y are defined in an area of the sheet heating unit which is adjacent to an atomizing surface of a porous body to improve the resistance of the area.

Figure 36:
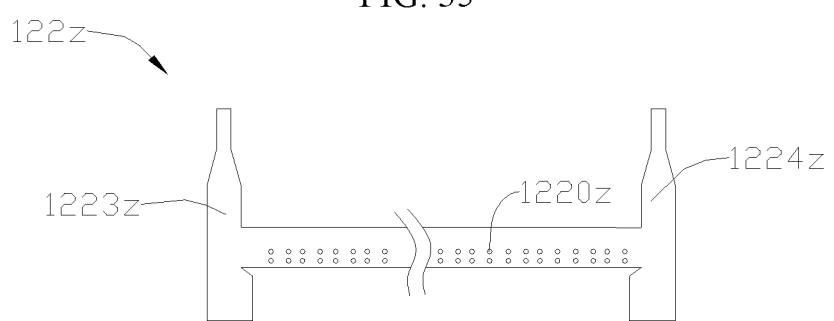
FIG. 36 is a schematic view of the heater of the heating assembly of FIG. 18 in a second alternative solution.

In FIG. 36, a heater 122z in some embodiments is shown. The heater 122z includes an elongated sheet heating unit in the middle and two electrical connecting units 1223z and 1224z respectively integrally connected with two ends of the heating unit. As an alternative solution for the heater 122p mentioned above, the difference between the heating heaters 122z and 122p lies in that, many through holes or blind holes 1220z are defined in an area of the heating unit of the heater 122z which is away from an atomizing surface of a porous body to improve the resistance of the area.

It can be understood that although the alternative solutions of the heater and the porous body in the above mentioned embodiments mainly elaborate the difference from those in the embodiments pre-mentioned, if they are not contradictory, they can replace with each other. For example, the heater in any embodiment above mentioned can cooperate with the porous body in any embodiment and any heating assembly above mentioned can be applied into the electronic cigarette.

What mentioned above are only the embodiments of the present disclosure, which are not to limit the scope of the patent of the present disclosure. Any equivalent structure or equivalent transformation of the procedure made with the specification and the pictures attached of the present disclosure, or directly or indirectly using the specification and the pictures attached of the present disclosure into other relevant technical fields, is included in the scope of the patent protection of the present disclosure.

What is claimed is:

1. An electronic cigarette atomizer, comprising an atomization assembly and a liquid reservoir engaging with the atomization assembly; the liquid reservoir comprising a liquid storage cavity;
   wherein the atomization assembly comprises a lower holder, an upper holder, and a heating assembly located between the lower holder and the upper holder; the heating assembly comprises a porous body and at least one heater engaging with the porous body;
   wherein the porous body has an atomizing surface and a liquid-absorbing surface, and the liquid-absorbing; surface and the atomizing surface are respectively located on two opposite sides of the porous body; the liquid-absorbing surface is in fluid communication with the liquid storage cavity, and an atomization cavity is formed between the atomizing surface and the lower holder; and
   wherein the upper holder comprises a main body, at least one liquid channel fluidly communicating the liquid-absorbing surface with the liquid storage cavity, and an exhaust channel disposed on the main body and fluidly communicating the atomization cavity with the outside.

2. The electronic cigarette atomizer of claim 1, wherein the lower holder is clamped with the upper holder.

3. The electronic cigarette atomizer of claim 1, wherein the upper holder is sleeved outside the heating assembly.

4. The electronic cigarette atomizer of claim 1, wherein the upper holder comprises at least one liquid channel which fluidly communicates the liquid-absorbing surface with the liquid storage cavity.

5. The electronic cigarette atomizer of claim 1, wherein the upper holder comprises an exhaust channel which is in fluid communication with the atomization cavity.

6. The electronic cigarette atomizer of claim 1, wherein the upper holder comprises at least one hook extending downwards to be hooked onto the lower holder.

7. The electronic cigarette atomizer of claim 1, wherein the upper holder has a length direction and a width direction, and the upper holder comprises two hooks extending downwards and arranged oppositely along the length direction of the upper holder.

8. The electronic cigarette atomizer of claim 1, wherein the upper holder comprises an embedded portion extending downward to be sleeved outside the heating assembly.

9. The electronic cigarette atomizer of claim 8, wherein the lower holder comprises a first supporting arm and a second supporting arm, and the embedded portion is arranged between the first supporting arm and the second supporting arm.

10. The electronic cigarette atomizer of claim 8, wherein the upper holder comprises two hooks extending downward and arranged spaced, and the embedded portion is arranged between the two hooks.

11. The electronic cigarette atomizer of claim 1, wherein the upper holder comprises two liquid channels respectively located on two opposite sides of the exhaust channel.

12. The electronic cigarette atomizer of claim 1, wherein the upper holder has a length direction and a width direction, and the at least one liquid channel and the exhaust channel are arranged along the length direction of the upper holder.

13. The electronic cigarette atomizer of claim 1, wherein the lower holder supports the upper holder.

14. The electronic cigarette atomizer of claim 1, wherein the lower holder supports the heating assembly.

15. The electronic cigarette atomizer of claim 1, wherein the lower holder comprises at least one electrode.

16. The electronic cigarette atomizer of claim 1, wherein the lower holder comprises a base and at least one supporting structure arranged on the base; the atomizing surface faces the base directly, a space is formed between the atomizing surface and the base, and the space forms the atomization cavity.

17. The electronic cigarette atomizer of claim 16, wherein the at least one supporting structure supports the upper holder.

18. The electronic cigarette atomizer of claim 16, wherein the at least one supporting structure supports the heating assembly.

19. The electronic cigarette atomizer of claim 16, wherein the base is clamped with the liquid reservoir.

20. The electronic cigarette atomizer of claim 16, wherein the base has a length direction and a width direction, and two ends along the length direction of the base are respectively clamped with the liquid reservoir.

21. The electronic cigarette atomizer of claim 16, wherein at least one electrode is provided on the base.

22. The electronic cigarette atomizer of claim 16, wherein the at least one supporting structure comprises a first supporting arm arranged on a top surface of the base and a second supporting arm arranged on a top surface of the base and opposite to the first supporting arm.

23. The electronic cigarette atomizer of claim 22, wherein the heating assembly is arranged between the first supporting arm and the second supporting arm.

24. The electronic cigarette atomizer of claim 22, wherein the base has a length direction and a width direction, and the first supporting arm and the second supporting arm are respectively arranged at two ends along the length direction of the base.

25. The electronic cigarette atomizer of claim 22, wherein the first supporting arm and the second supporting arm are respectively clamped with the upper holder.

26. The electronic cigarette atomizer of claim 22, wherein outer sides of the first supporting arm and the second supporting arm are respectively provided with clamping portions used for being clamped to the upper holder.

27. The electronic cigarette atomizer of claim 22, wherein the base is provided with at least one electrode, and the at least one electrode is arranged between the first supporting arm and the second supporting arm.

28. The electronic cigarette atomizer of claim 22, wherein inner sides of top ends of the first supporting arm and the second supporting arm are respectively recessed to form containing grooves, and the containing grooves respectively form steps on the first supporting arm and the second supporting arm, and the heating assembly is disposed on the steps.

29. An electronic cigarette, comprising an electronic cigarette atomizer which comprises an atomization assembly and a liquid reservoir engaging with the atomization assembly; the liquid reservoir comprising a liquid storage cavity;
wherein the atomization assembly comprises a lower holder, an upper holder, and a heating assembly located between the lower holder and the upper holder; the heating assembly comprises a porous body and at least one heater engaging with the porous body, and
wherein the porous body has an atomizing face and a liquid-absorbing surface, and the liquid-absorbing surface and the atomizing surface are respectively located on two opposite sides of the porous body in a height direction of the atomization assembly; the liquid-absorbing surface faces upwardly and is in fluid communication with the liquid storage cavity, the atomizing face faces downwardly, and an atomization cavity is formed between the atomizing surface and the lower holder; and
wherein the liquid reservoir is sleeved on the upper holder.

30. The electronic cigarette of claim 29, wherein the upper holder is sleeved outside the heating assembly.

31. The electronic cigarette of claim 29, wherein the upper holder comprises a main body, at least one liquid channel fluidly communicating the liquid-absorbing surface with the liquid storage cavity, and an exhaust channel disposed on the main body and fluidly communicating the atomization cavity with the outside.

32. The electronic cigarette of claim 29, wherein the lower holder comprises at least one electrode.

33. The electronic cigarette of claim 29, wherein the lower holder comprises a base and at least one supporting structure arranged on the base; the atomizing surface faces the base directly, a space is formed between the atomizing surface and the base, and the space forms the atomization cavity.

\* \* \* \* \*